US005521086A

United States Patent [19]
Scott et al.

[11] Patent Number: 5,521,086
[45] Date of Patent: May 28, 1996

[54] SECRETION SEQUENCE FOR THE PRODUCTION OF A HETEROLOGOUS PROTEIN IN YEAST

[75] Inventors: Richard W. Scott, Wallingford; Russell A. Brierley, West Chester; David S. Howland, Exton, all of Pa.

[73] Assignee: Cephalon, Inc., West Chester, Pa.

[21] Appl. No.: 122,889

[22] Filed: Sep. 16, 1993

[51] Int. Cl.$^6$ ............................... C12N 1/19; C12N 1/21; C12N 15/62
[52] U.S. Cl. .................... 435/254.2; 435/252.3; 435/252.33; 435/254.23; 435/172.3; 435/69.1; 435/69.7; 536/23.4
[58] Field of Search ..................... 435/69.7, 254.23, 435/320.1, 252.3, 252.33, 254.2, 69.1, 172.3; 536/23.4; 530/350

[56] References Cited

U.S. PATENT DOCUMENTS

| | | | |
|---|---|---|---|
| 4,546,082 | 10/1985 | Kurjan et al. | 435/172.3 |
| 4,870,008 | 9/1989 | Brake | 435/69.1 |
| 4,963,665 | 10/1990 | Rotwein et al. | 536/23.51 |
| 5,070,075 | 12/1991 | Rotwein et al. | 514/12 |

FOREIGN PATENT DOCUMENTS

| | | |
|---|---|---|
| 0123228A2 | 10/1984 | European Pat. Off. . |
| 0495208A2 | 7/1992 | European Pat. Off. . |
| 60-233371 | 5/1991 | Japan . |
| WO86/00637 | 1/1986 | WIPO . |
| WO90/01063 | 2/1990 | WIPO . |
| WO90/10075 | 9/1990 | WIPO . |
| WO92/04363 | 3/1992 | WIPO . |

OTHER PUBLICATIONS

Andrews et al., "Sequences beyond the Cleavage Site Influence Signal Peptide Function," The Journal of Biological Chemistry 263:15791–15798, 1988.

Bayne et al., "Expression, purification and characterization of recombinant human insulin–like growth factor I in yeast," Gene 66:234–244, 1988.

Bos et al., "$NH_2$–terminal hydrophobic region of influenza virus neuraminidase provides the signal function in translocation," Proc. Natl. Acad. Sci. USA 81:2327–2331, 1984.

Bonatti et al., "Absence of a Cleavable Signal Sequence in Sindbis Virus Glycoprotein $PE_2$," The Journal of Biological Chemistry 254:12261–12264, 1979.

Chaudhuri et al., "The pro–region of the yeast prepro–α–factor is essential for membrane–translocation of human insulin–like growth factor 1 in vivo," Eur. J. Biochem. 206:793–800, 1992.

Clare et al., "High–level Expression of Tetanus Toxin Fragment C in *Pichia pastoris* Strains Containing Multiple Tandem Integrations of the Gene," Bio/Technology 9:455–460, 1991.

Clements et al., "Secretion of human epidermal growth factor from *Saccharomyces cerevisiae* using synthetic leader sequences," Gene 106:267–272, 1991.

Degryse et al., "Addition of a dipeptide spacer significantly improves secretion of ovine trophoblast interferon in yeast," Gene 118:47–53, 1992.

Kohara et al., "Alteration of N–terminal Residues of Mature Human Lysozyme Affects Its Secretion in Yeast and Translocation into Canine Microsomal Vesicles," The Journal of Biological Chemistry 266:20363–20368, 1991.

Meyack et al., "Two yeast acid phosphatase structural genes . . . in their promoter and coding sequences," The EMBO Journal 6:675–680, 1982.

Palmiter et al., "Ovalbumin: A secreted protein without a transient hydrophobic leader sequence," Proc. Natl. Acad. Sci. USA 75:94–98, 1978.

Sleep et al., "The Secretion of Human Serum Albumin from the Yeast *Saccharomyces cerevisiae* Using Five Different Leader Sequences," Bio/Technology 8:42–46, 1990.

Strom, et al., "Mapping of Export Signals of *Pseudomonas aeruginosa* Pilin with Alkaline Phosphatase Fusions," Journal of Bacteriology 169:3181–3188, 1987.

Zsebo et al., "Protein Secretion from *Saccharomyces cerevisiae* Directed by the Prepro–α–factor Leader Region," The Journal of Biological Chemistry 261:5858–5865, 1986.

Primary Examiner—Nancy T. Vogel
Attorney, Agent, or Firm—Fish & Richardson

[57] ABSTRACT

The invention generally features a novel recombinant DNA molecule useful for producing a heterologous protein, e.g., insulin–like growth factor-I, in yeast. The DNA molecule includes the following sequences joined in frame and in the following 5' to 3' progression: a sequence encoding a signal peptide of a yeast secreted protein; a sequence encoding at least 5 amino acids of the N-terminal region of a mature acid phosphatase protein, a sequence encoding a heterologous protein. Preferably the DNA molecule also encodes a spacer element that includes a proteolytic cleavage site.

18 Claims, 16 Drawing Sheets

PSS

```
ATG TTC TCT CCA ATT TTC TCC TTG GAA ATT ATT TTA GCT TTG GCT
 M   F   S   P   I   F   S   L   E   I   I   L   A   L   A
PHO signal ──────────────────────────────────────────────────▶

ACT TTG CAA TCT GTC TTC GCT - GGA CCG GAG ACG CTC TGC... ...
 T   L   Q   S   V   F   A ◊  G   P   E   T   L   C  .   .
──────────────────────────▶   IGF-I ─────────────────── ── ─▶
```

PPI

```
ATG TTC TCT CCA ATT TTC TCC TTG GAA ATT ATT TTA GCT TTG GCT
 M   F   S   P   I   F   S   L   E   I   I   L   A   L   A
PHO signal ──────────────────────────────────────────────────▶

ACT TTG CAA TCT GTC TTC GCT - GTT GAG TTG CAG CAC GTT CTT
 T   L   Q   S   V   F   A ◊  V   E   L   Q   H   V   L
──────────────────────────▶   SFE ──────────────────────────▶

GGA GTC AAC GAC AGA TCC TAT CCT CAG AGG ACA GAT GAT CAG TAC
 G   V   N   D   R   P   Y   P   Q   R   T   D   D   Q   Y

AAC ATT CTG - GAG AAG CGT - GGA CCG GAG ACG CTC TGC... ...
 N   I   L ◊  E   K   R  ◊  G   P   E   T   L   C  .   .
         ─▶  spacer ─▶ IGF-I ─────────────────── ── ─▶
```

PKV

```
ATG TTC TCT CCA ATT TTC TCC TTG GAA ATT ATT TTA GCT TTG GCT
 M   F   S   P   I   F   S   L   E   I   I   L   A   L   A
PHO signal ──────────────────────────────────────────────────▶

ACG TTG CAA TCT GTC TTC GCT - TTG GAG CAT ACT CAT CGA AGA
 T   L   Q   S   V   F   A ◊  L   E   H   T   H   R   R
──────────────────────────▶   K. lactis killer pro ─────────▶

GGC TCC TTA GTC AAA AGA - GGA CCG GAG ACG CTC TGC... ...
 G   S   L   V   K   R ◊  G   P   E   T   L   C  .   .
────────────────────────▶ IGF-I ─────────────────── ── ─▶
```

FIG. 3A

PKD

ATG TTC TCT CCA ATT TTC TCC TTG GAA ATT ATT TTA GCT TTG GCT
M   F   S   P   I   F   S   L   E   I   I   L   A   L   A
PHO signal ───────────────────────────────────────────────▶

ACT TTG CAA TCT GTC TTC GCT - TTG GAG CAT ACT CAT CGA AGA
T   L   Q   S   V   F   A ◇ L   E   H   T   H   R   R
──────────────────────────▶ K. lactis killer pro-D ──────▶

GGC TCC TTA GAT AAA AGA - GGA CCG GAG ACG CTC TGC . . . . . .
G   S   L   D   K   R ◇ G   P   E   T   L   C   .   .
─────────────────────▶ IGF-I ──────────────── ── ── ──▶

AM5

ATG TTC TCT CCA ATT TTC TCC TTG GAA ATT ATT TTA GCT TTG GCT
M   F   S   P   I   F   S   L   E   I   I   L   A   L   A
PHO signal ───────────────────────────────────────────────▶

ACT TTG CAA TCT GTC TTC GCT - TCC TTA GTC AAA AGA - GGA CCG
T   L   Q   S   V   F   A ◇ S   L   D   K   R ◇ G   P
──────────────────────────▶ SLDKR pro ──────▶ IGF-I ──▶

GAG ACG CTC TGC . . . . . .
E   T   L   C   .   .
─────────────── ── ──▶

PPSI

ATG TTC TCT CCA ATT TTC TCC TTG GAA ATT ATT TTA GCT TTG GCT
M   F   S   P   I   F   S   L   E   I   I   L   A   L   A
PHO signal ───────────────────────────────────────────────▶

ACT TTG CAA TCT GTC TTC GCT - GTT GAG TTG CAG CAC GTT CTT
T   L   Q   S   V   F   A ◇ V   E   L   Q   H   V   L
──────────────────────────▶ SFE ────────▶

GGA GTC AAC GAC AGA TCC TAT CCT CAG AGG ACA GAT GAT CAG TAC
G   V   N   D   R   P   Y   P   Q   R   T   D   D   Q   Y
───────────────────────────────────────────────────────────▶

FIG. 3B

```
AAC ATT CTG - GAG AAG CGT TCT TTG GAC AAG AGA - GGA CCG GAG
 N   I   L ◊  E   K   R   S   L   D   K   R  ◊  G   P   E
─────────▶    spacer ─────────────────────────▶ IGF-I ──────▶
ACG CTC TGC ... ...
 T   L   C    .   .
──────────────────▶
```

PPEAI

```
ATG TTC TCT CCA ATT TTC TCC TTG GAA ATT ATT TTA GCT TTG GCT
 M   F   S   P   I   F   S   L   E   I   I   L   A   L   A
PHO signal ─────────────────────────────────────────────────▶

ACT TTG CAA TCT GTC TTC GCT - GTT GAG TTG CAG CAC GTT CTT
 T   L   Q   S   V   F   A ◊ V   E   L   Q   H   V   L
───────────────────────────▶ SFE ───────────────────────▶

GGA GTC AAC GAC AGA TCC TAT CCT CAG AGG ACA GAT GAT CAG TAC
 G   V   N   D   R   P   Y   P   Q   R   T   D   D   Q   Y
────────────────────────────────────────────────────────────▶

AAC ATT CTG - GAG AAG CGT GAG GCT - GGA CCG GAG ACG CTC...
 N   I   L ◊  E   K   R   E   A  ◊  G   P   E   T   L   .
──────────▶   spacer ──────────────▶ IGF-I ─────────────────▶
```

INV

```
ATG CTT TTG CAA GCT TTC CTT TTC CTT TTG GCT GGT TTT GCA GCC
 M   L   L   Q   A   F   L   F   L   L   A   G   F   A   A
INV signal ─────────────────────────────────────────────────▶

AAA ATA TCT GCA - GGA CCG GAG ACG CTC TGC ... ...
 K   I   S   A ◊  G   P   E   T   L   C    .   .
──────────────▶   IGF-I ─────────────────────▶
```

FIG. 3C

INVS

ATG CTT TTG CAA GCT TTC CTT TTC CTT TTG GCT GGT TTT GCA GCC
 M   L   L   Q   A   F   L   F   L   L   A   G   F   A   A
*INV signal* ─────────────────────────────────────────────────▶

AAA ATA TCT GCA - TCT TTG GAC AAG AGA - GGA CCG GAG ACG ...
 K   I   S   A ◇ S   L   D   K   R ◇ G   P   E   T  . .
 ─────────▶   *SLDKR pro* ─────▶   *IGF-I* ─────── ── ─▶

HSA

ATG AAG TGG GTA ACC TTT ATT TCC CTT CTT TTT CTC TTT AGC TCG
 M   K   W   V   T   F   I   S   L   L   F   L   F   S   S
*HSA signal* ─────────────────────────────────────────────────▶

GCT TAT TCC - AGG GGT GTG TTT CGT CGA - GGA CCG GAG ACG ...
 A   Y   S ◇ R   G   V   F   R   R ◇ G   P   E   T  . .
 ─────────▶   *HSA pro* ─────────▶   *IGF-I* ─────── ── ─▶

FIG. 3D

REACTION 1　　　　　　　REACTION 2
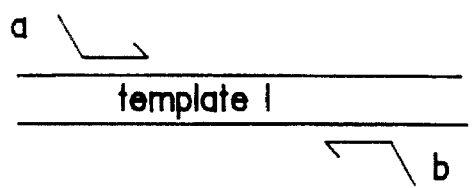 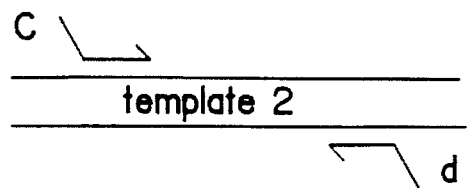
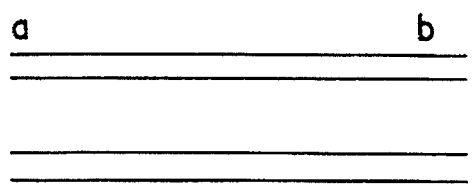 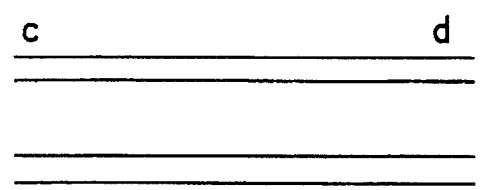
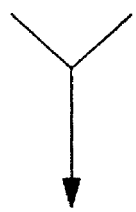
COMBINE, DENATURE, RE-ENNEAL
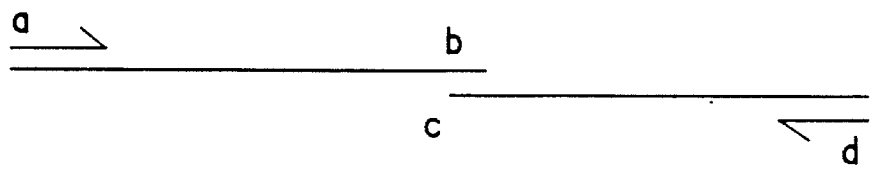
PCR AMPLIFY
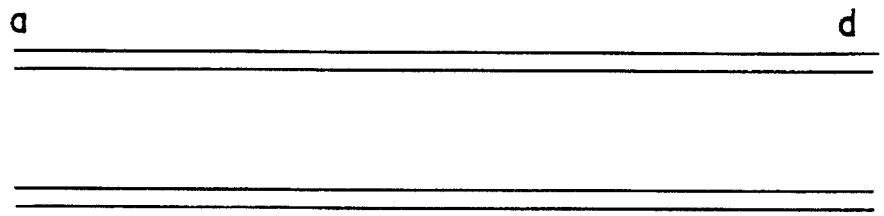
FIG. 6

SEQUENCE LISTING ( 1 ) GENERAL INFORMATION:

( i i i ) NUMBER OF SEQUENCES: 44

( 2 ) INFORMATION FOR SEQ ID NO: 1:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 1:

GCCGAATTCA TGTTCTCTCC AATTTTCTCC TTG    33

( 2 ) INFORMATION FOR SEQ ID NO: 2:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 2:

GAGCGTCTCC GGTCCAGCGA AGACAGATTG CAA    33

( 2 ) INFORMATION FOR SEQ ID NO: 3:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 3:

CAATCTGTCT TCGCTGGACC GGAGACGCTC TGC    33

( 2 ) INFORMATION FOR SEQ ID NO: 4:

( i ) SEQUENCE CHARACTERISTICS:
( A ) LENGTH: 35
( B ) TYPE: nucleic acid
( C ) STRANDEDNESS: single
( D ) TOPOLOGY: linear ( x i ) SEQUENCE DESCRIPTION: SEQ ID NO: 4:

CTAGAATTCT TATCAAGCTG ACTTGGCAGG CTTGA    35

( 2 ) INFORMATION FOR SEQ ID NO: 5:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( x i ) SEQUENCE DESCRIPTION: SEQ ID NO: 5:

GTGCTGCAAC TCAACAGCGA AGACAGATTG CAA    33

( 2 ) INFORMATION FOR SEQ ID NO: 6:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CAATCTGTCT TCGCTGTTGA GTTGCAGCAC GTT    33

( 2 ) INFORMATION FOR SEQ ID NO: 7:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GAGCGTCTCC GGTCCACGCT TCTCCAGAAT GTTGTACTG    39

( 2 ) INFORMATION FOR SEQ ID NO: 8:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 8:

ATTCTGGAGA AGCGTGGACC GGAGACGCTC TGC    33

( 2 ) INFORMATION FOR SEQ ID NO: 9:

( i ) SEQUENCE CHARACTERISTICS:
        ( A ) LENGTH: 45
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GGAGCCTCTT CGATGAGTAT GCTCCAAAGC GAAGACAGAT TGCAA    45

( 2 ) INFORMATION FOR SEQ ID NO: 10:

( i ) SEQUENCE CHARACTERISTICS:
        ( A ) LENGTH: 45
        ( B ) TYPE: nucleic acid
        ( C ) STRANDEDNESS: single
        ( D ) TOPOLOGY: linear ( x i ) SEQUENCE DESCRIPTION: SEQ ID NO: 10:

CATCGAAGAG GCTCCTTAGT CAAAAGAGGA CCGGAGACGC TCTGC    45

( 2 ) INFORMATION FOR SEQ ID NO: 11:

( i ) SEQUENCE CHARACTERISTICS:

(A) LENGTH: 45
        (B) TYPE: nucleic acid
        (C) STRANDEDNESS: single
        (D) TOPOLOGY: linear (x i) SEQUENCE DESCRIPTION: SEQ ID NO: 11:

CATCGAAGAG GCTCCTTAGA TAAAAGAGGA CCGGAGACGC TCTGC                45

(2) INFORMATION FOR SEQ ID NO: 12:

(i) SEQUENCE CHARACTERISTICS:
        (A) LENGTH: 33
        (B) TYPE: nucleic acid
        (C) STRANDEDNESS: single
        (D) TOPOLOGY: linear (x i) SEQUENCE DESCRIPTION: SEQ ID NO: 12:

TCTTTTATCT AAGGAAGCGA AGACAGATTG CAA                              33

(2) INFORMATION FOR SEQ ID NO: 13:

(i) SEQUENCE CHARACTERISTICS:
        (A) LENGTH: 33
        (B) TYPE: nucleic acid
        (C) STRANDEDNESS: single
        (D) TOPOLOGY: linear (x i) SEQUENCE DESCRIPTION: SEQ ID NO: 13:

TCCTTAGATA AAGAGGACC GGAGACGCTC TGC                               33

(2) INFORMATION FOR SEQ ID NO: 14:

(i) SEQUENCE CHARACTERISTICS:
        (A) LENGTH: 34
        (B) TYPE: nucleic acid
        (C) STRANDEDNESS: single
        (D) TOPOLOGY: linear (x i) SEQUENCE DESCRIPTION: SEQ ID NO: 14:

TCTCTTGTCC AAAGAACGCT TCTCCAGAAT GTTG                             34

(2) INFORMATION FOR SEQ ID NO: 15:

(i) SEQUENCE CHARACTERISTICS:
        (A) LENGTH: 33
        (B) TYPE: nucleic acid
        (C) STRANDEDNESS: single
        (D) TOPOLOGY: linear (x i) SEQUENCE DESCRIPTION: SEQ ID NO: 15:

TCTTTGGACA AGAGAGGACC GGAGACGCTC TGC                              33

(2) INFORMATION FOR SEQ ID NO: 16:

(i) SEQUENCE CHARACTERISTICS:
        (A) LENGTH: 42
        (B) TYPE: nucleic acid
        (C) STRANDEDNESS: single
        (D) TOPOLOGY: linear (x i) SEQUENCE DESCRIPTION: SEQ ID NO: 16:

GAGCGTCTCC GGTCCAGCCT CACGCTTCTC CAGAATGTTG TA                    42

(2) INFORMATION FOR SEQ ID NO: 17:

(i) SEQUENCE CHARACTERISTICS:
        (A) LENGTH: 39
        (B) TYPE: nucleic acid ( C ) STRANDEDNESS: single
( D ) TOPOLOGY: linear ( x i ) SEQUENCE DESCRIPTION: SEQ ID NO: 17:

ATTCTGGAGA AGCGTGAGGC TGGACCGGAG ACGCTCTGC 39

( 2 ) INFORMATION FOR SEQ ID NO: 18:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 18:

GGCGAATTCA TGCTTTTGCA AGCTTTCCTT TTC 33

( 2 ) INFORMATION FOR SEQ ID NO: 19:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 19:

GAGCGTCTCC GGTCCTGCAG ATATTTGGC TGC 33

( 2 ) INFORMATION FOR SEQ ID NO: 20:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 20:

GGACCGGAGA CGCTCTGCGG GGCT 24

( 2 ) INFORMATION FOR SEQ ID NO: 21:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 21:

TCTTTTATCT AAGGATGCAG ATATTTGGC TGC 33

( 2 ) INFORMATION FOR SEQ ID NO: 22:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 22:

GGCGAATTCA TGAAGTGGGT AACCTTTATT TCC 33

( 2 ) INFORMATION FOR SEQ ID NO: 23:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 23:

GAGCGTCTCC GGTCCTCGAC GAAACACACC CCT                33

( 2 ) INFORMATION FOR SEQ ID NO: 24:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( x i ) SEQUENCE DESCRIPTION: SEQ ID NO: 24:

```
Glu  Lys  Arg  Ser  Leu  Asp  Lys  Arg
1                   5
```

( 2 ) INFORMATION FOR SEQ ID NO: 25:

( i ) SEQUENCE CHARACTERISTICS:
        ( A ) LENGTH: 84
        ( B ) TYPE: nucleic acid
        ( C ) STRANDEDNESS: double
        ( D ) TOPOLOGY: linear ( x i ) SEQUENCE DESCRIPTION: SEQ ID NO: 25:

```
ATG  TTC  TCT  CCA  ATT  TTG  TCC  TTG  GAA  ATT  ATT  TTA  GCT  TTG  GCT  ACT    48
Met  Phe  Ser  Pro  Ile  Leu  Ser  Leu  Glu  Ile  Ile  Leu  Ala  Leu  Ala  Thr
1                   5                        10                       15

TTG  CAA  TCT  GTC  TTC  GCT  GGA  CCG  GAG  ACG  CTC  TGC                         84
Leu  Gln  Ser  Val  Phe  Ala  Gly  Pro  Glu  Thr  Leu  Cys
                    20                       25
```

( 2 ) INFORMATION FOR SEQ ID NO: 26:

( i ) SEQUENCE CHARACTERISTICS:
        ( A ) LENGTH: 168
        ( B ) TYPE: nucleic acid
        ( C ) STRANDEDNESS: double
        ( D ) TOPOLOGY: linear ( x i ) SEQUENCE DESCRIPTION: SEQ ID NO: 26:

```
ATG  TTC  TCT  CCA  ATT  TTG  TCC  TTG  GAA  ATT  ATT  TTA  GCT  TTG  GCT  ACT    48
Met  Phe  Ser  Pro  Ile  Leu  Ser  Leu  Glu  Ile  Ile  Leu  Ala  Leu  Ala  Thr
1                   5                        10                       15

TTG  CAA  TCT  GTC  TTC  GCT  GTT  GAG  TTG  CAG  CAC  GTT  CTT  GGA  GTC  AAC    96
Leu  Gln  Ser  Val  Phe  Ala  Val  Glu  Leu  Gln  His  Val  Leu  Gly  Val  Asn
                    20                       25                       30

GAC  AGA  TCC  TAT  CCT  CAG  AGG  ACA  GAT  GAT  CAG  TAC  AAC  ATT  CTG  GAG   144
Asp  Arg  Ser  Tyr  Pro  Gln  Arg  Thr  Asp  Asp  Gln  Tyr  Asn  Ile  Leu  Glu
                    35                       40                       45

AAG  CGT  GGA  CCG  GAG  ACG  CTC  TGC                                            168
Lys  Arg  Gly  Pro  Glu  Thr  Leu  Cys
50                       55
```

( 2 ) INFORMATION FOR SEQ ID NO: 27:

( i ) SEQUENCE CHARACTERISTICS:
        ( A ) LENGTH: 123
        ( B ) TYPE: nucleic acid
        ( C ) STRANDEDNESS: double
        ( D ) TOPOLOGY: linear ( x i ) SEQUENCE DESCRIPTION: SEQ ID NO: 27:

```
ATG  TTC  TCT  CCA  ATT  TTG  TCC  TTG  GAA  ATT  ATT  TTA  GCT  TTG  GCT  ACG    48
Met  Phe  Ser  Pro  Ile  Leu  Ser  Leu  Glu  Ile  Ile  Leu  Ala  Leu  Ala  Thr
1                   5                        10                       15
```

```
TTG CAA TCT GTC TTC GCT TTG GAG CAT ACT CAT CGA AGA GGC TCC TTA        96
Leu Gln Ser Val Phe Ala Leu Glu His Thr His Arg Arg Gly Ser Leu
            20                  25                      30

GTC AAA AGA GGA CCG GAG ACG CTC TGC                                   123
Val Lys Arg Gly Pro Glu Thr Leu Cys
        35                  40
```

( 2 ) INFORMATION FOR SEQ ID NO: 28:

( i ) SEQUENCE CHARACTERISTICS:
        ( A ) LENGTH: 123
        ( B ) TYPE: nucleic acid
        ( C ) STRANDEDNESS: double
        ( D ) TOPOLOGY: linear ( x i ) SEQUENCE DESCRIPTION: SEQ ID NO: 28:

```
ATG TTC TCT CCA ATT TTG TCC TTG GAA ATT ATT TTA GCT TTG GCT ACT        48
Met Phe Ser Pro Ile Leu Ser Leu Glu Ile Ile Leu Ala Leu Ala Thr
1               5                   10                      15

TTG CAA TCT GTC TTC GCT TTG GAG CAT ACT CAT CGA AGA GGC TCC TTA        96
Leu Gln Ser Val Phe Ala Leu Glu His Thr His Arg Arg Gly Ser Leu
            20                  25                      30

GAT AAA AGA GGA CCG GAG ACG CTC TGC                                   123
Asp Lys Arg Gly Pro Glu Thr Leu Cys
        35                  40
```

( 2 ) INFORMATION FOR SEQ ID NO: 29:

( i ) SEQUENCE CHARACTERISTICS:
        ( A ) LENGTH: 99
        ( B ) TYPE: nucleic acid
        ( C ) STRANDEDNESS: double
        ( D ) TOPOLOGY: linear ( x i ) SEQUENCE DESCRIPTION: SEQ ID NO: 29:

```
ATG TTC TCT CCA ATT TTG TCC TTG GAA ATT ATT TTA GCT TTG GCT ACT        48
Met Phe Ser Pro Ile Leu Ser Leu Glu Ile Ile Leu Ala Leu Ala Thr
1               5                   10                      15

TTG CAA TCT GTC TTC GCT TCC TTA GTC AAA AGA GGA CCG GAG ACG CTC        96
Leu Gln Ser Val Phe Ala Ser Leu Val Lys Arg Gly Pro Glu Thr Leu
            20                  25                      30

TGC                                                                    99
Cys
```

( 2 ) INFORMATION FOR SEQ ID NO: 30:

( i ) SEQUENCE CHARACTERISTICS:
        ( A ) LENGTH: 183
        ( B ) TYPE: nucleic acid
        ( C ) STRANDEDNESS: double
        ( D ) TOPOLOGY: linear ( x i ) SEQUENCE DESCRIPTION: SEQ ID NO: 30:

```
ATG TTC TCT CCA ATT TTG TCC TTG GAA ATT ATT TTA GCT TTG GCT ACT        48
Met Phe Ser Pro Ile Leu Ser Leu Glu Ile Ile Leu Ala Leu Ala Thr
1               5                   10                      15

TTG CAA TCT GTC TTC GCT GTT GAG TTG CAG CAC GTT CTT GGA GTC AAC        96
Leu Gln Ser Val Phe Ala Val Glu Leu Gln His Val Leu Gly Val Asn
            20                  25                      30

GAC AGA TCC TAT CCT CAG AGG ACA GAT GAT CAG TAC AAC ATT CTG GAG       144
Asp Arg Ser Tyr Pro Gln Arg Thr Asp Asp Gln Tyr Asn Ile Leu Glu
        35                  40                      45

AAG CGT TCT TTG GAC AAG AGA GGA CCG GAG ACG CTC TGC                   183
Lys Arg Ser Leu Asp Lys Arg Gly Pro Glu Thr Leu Cys
        50                  55                  60
```

( 2 ) INFORMATION FOR SEQ ID NO: 31:

( i ) SEQUENCE CHARACTERISTICS:
( A ) LENGTH: 171
( B ) TYPE: nucleic acid
( C ) STRANDEDNESS: double
( D ) TOPOLOGY: linear ( x i ) SEQUENCE DESCRIPTION: SEQ ID NO: 31:

| ATG | TTC | TCT | CCA | ATT | TTG | TCC | TTG | GAA | ATT | ATT | TTA | GCT | TTG | GCT | ACT | 48 |
|-----|-----|-----|-----|-----|-----|-----|-----|-----|-----|-----|-----|-----|-----|-----|-----|-----|
| Met | Phe | Ser | Pro | Ile | Leu | Ser | Leu | Glu | Ile | Ile | Leu | Ala | Leu | Ala | Thr | |
| 1   |     |     |     | 5   |     |     |     |     | 10  |     |     |     |     | 15  |     | |

| TTG | CAA | TCT | GTC | TTC | GCT | GTT | GAG | TTG | CAG | CAC | GTT | CTT | GGA | GTC | AAC | 96 |
|-----|-----|-----|-----|-----|-----|-----|-----|-----|-----|-----|-----|-----|-----|-----|-----|-----|
| Leu | Gln | Ser | Val | Phe | Ala | Val | Glu | Leu | Gln | His | Val | Leu | Gly | Val | Asn | |
|     |     |     | 20  |     |     |     |     | 25  |     |     |     |     | 30  |     |     | |

| GAC | AGA | TCC | TAT | CCT | CAG | AGG | ACA | GAT | GAT | CAG | TAC | AAC | ATT | CTG | GAG | 144 |
|-----|-----|-----|-----|-----|-----|-----|-----|-----|-----|-----|-----|-----|-----|-----|-----|-----|
| Asp | Arg | Ser | Tyr | Pro | Gln | Arg | Thr | Asp | Asp | Gln | Tyr | Asn | Ile | Leu | Glu | |
|     |     | 35  |     |     |     |     | 40  |     |     |     |     | 45  |     |     |     | |

| AAG | CGT | GAG | GCT | GGA | CCG | GAG | ACG | CTC | | | | | | | | 171 |
|-----|-----|-----|-----|-----|-----|-----|-----|-----|---|---|---|---|---|---|---|-----|
| Lys | Arg | Glu | Ala | Gly | Pro | Glu | Thr | Leu | | | | | | | | |
|     | 50  |     |     |     |     | 55  |     |     | | | | | | | | |

( 2 ) INFORMATION FOR SEQ ID NO: 32:

( i ) SEQUENCE CHARACTERISTICS:
( A ) LENGTH: 75
( B ) TYPE: nucleic acid
( C ) STRANDEDNESS: double
( D ) TOPOLOGY: linear ( x i ) SEQUENCE DESCRIPTION: SEQ ID NO: 32:

| ATG | CTT | TTG | CAA | GCT | TTC | CTT | TTC | CTT | TTG | GCT | GGT | TTT | GCA | GCC | AAA | 48 |
|-----|-----|-----|-----|-----|-----|-----|-----|-----|-----|-----|-----|-----|-----|-----|-----|-----|
| Met | Leu | Leu | Gln | Ala | Phe | Leu | Phe | Leu | Leu | Ala | Gly | Phe | Ala | Ala | Lys | |
| 1   |     |     |     | 5   |     |     |     |     | 10  |     |     |     |     | 15  |     | |

| ATA | TCT | GCA | GGA | CCG | GAG | ACG | CTC | TGC | | | | | | | | 75 |
|-----|-----|-----|-----|-----|-----|-----|-----|-----|---|---|---|---|---|---|---|-----|
| Ile | Ser | Ala | Gly | Pro | Glu | Thr | Leu | Cys | | | | | | | | |
|     |     |     | 20  |     |     |     |     | 25  | | | | | | | | |

( 2 ) INFORMATION FOR SEQ ID NO: 33:

( i ) SEQUENCE CHARACTERISTICS:
( A ) LENGTH: 84
( B ) TYPE: nucleic acid
( C ) STRANDEDNESS: double
( D ) TOPOLOGY: linear ( x i ) SEQUENCE DESCRIPTION: SEQ ID NO: 33:

| ATG | CTT | TTG | CAA | GCT | TTC | CTT | TTC | CTT | TTG | GCT | GGT | TTT | GCA | GCC | AAA | 48 |
|-----|-----|-----|-----|-----|-----|-----|-----|-----|-----|-----|-----|-----|-----|-----|-----|-----|
| Met | Leu | Leu | Gln | Ala | Phe | Leu | Phe | Leu | Leu | Ala | Gly | Phe | Ala | Ala | Lys | |
| 1   |     |     |     | 5   |     |     |     |     | 10  |     |     |     |     | 15  |     | |

| ATA | TCT | GCA | TCT | TTG | GAC | AAG | AGA | GGA | CCG | GAG | ACG | | | | | 84 |
|-----|-----|-----|-----|-----|-----|-----|-----|-----|-----|-----|-----|---|---|---|---|-----|
| Ile | Ser | Ala | Ser | Leu | Asp | Lys | Arg | Gly | Pro | Glu | Thr | | | | | |
|     |     |     | 20  |     |     |     |     | 25  |     |     |     | | | | | |

( 2 ) INFORMATION FOR SEQ ID NO: 34:

( i ) SEQUENCE CHARACTERISTICS:
( A ) LENGTH: 84
( B ) TYPE: nucleic acid
( C ) STRANDEDNESS: double
( D ) TOPOLOGY: linear ( x i ) SEQUENCE DESCRIPTION: SEQ ID NO: 34:

| ATG | AAG | TGG | GTA | ACC | TTT | ATT | TCC | CTT | CTT | TTT | CTC | TTT | AGC | TCG | GCT | 48 |
|-----|-----|-----|-----|-----|-----|-----|-----|-----|-----|-----|-----|-----|-----|-----|-----|-----|
| Met | Lys | Trp | Val | Thr | Phe | Ile | Ser | Leu | Leu | Phe | Leu | Phe | Ser | Ser | Ala | |
| 1   |     |     |     | 5   |     |     |     |     | 10  |     |     |     |     | 15  |     | |

| TAT TCC AGG GGT GTG TTT CGT CGA GGA CCG GAG ACG | 84 |
| Tyr Ser Arg Gly Val Phe Arg Arg Gly Pro Glu Thr | |
|      20                        25                | |

( 2 ) INFORMATION FOR SEQ ID NO:35:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

GCCGAATTCA TGTTCTCTCC A                       21

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

TCAGCTTGAT AAGAATTCTA G                       21

( 2 ) INFORMATION FOR SEQ ID NO:37:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

TGGAGAGAAC ATGAATTCGG C                       21

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

CTAGAATTCT TATCAAGCTG A                       21

( 2 ) INFORMATION FOR SEQ ID NO:39:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

AATTCATGTT CTCTCCA                            17

(2) INFORMATION FOR SEQ ID NO:40:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

TCAGCTTGAT AAG                                                    13

(2) INFORMATION FOR SEQ ID NO:41:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

TGGAGAGAAC ATG                                                    13

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

AATTCTTATC AAGCTGA                                          17

(2) INFORMATION FOR SEQ ID NO:43:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:43:

Glu  Lys  Arg  Glu  Ala
    1                    5

(2) INFORMATION FOR SEQ ID NO:44:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:44:

Ser  Leu  Asp  Lys  Arg
    1                    5

SECRETION SEQUENCE FOR THE PRODUCTION OF A HETEROLOGOUS PROTEIN IN YEAST

BACKGROUND OF THE INVENTION

The invention concerns the production of heterologous proteins in yeast.

Yeast organisms are favored for producing heterologous proteins by recombinant DNA technology due to their ability to secrete expressed proteins from the cell. Secretion of the produced protein has several advantages. First, secretion avoids cellular toxicity, which is often a problem when recombinant proteins accumulate inside the cell. Second, many proteins require passage through the secretory pathway in order to obtain proper conformational folding and full biological activity. Third, biochemical purification of the recombinant protein is facilitated by secretion since higher initial degrees of purity are obtained in the culture broth than in a cell lysate, and fewer purification steps are needed.

Transport of proteins through the cellular organelles of the secretory pathway is dependent in part on having an N-terminal secretion sequence. In yeast this sequence takes the form of a signal peptide which is synthesized as part of the precursor form of the protein. The signal peptide, removed by specific proteolytic cleavage during transit, is not part of the mature protein product. The signal peptide is found at the extreme N-terminus of the precursor form of the protein and mediates translocation of the nascent polypeptide into the lumen of the endoplasmic reticulum (Walter et al. 1984 *Cell* 38:5–8; Nicchitta et al. 1991 *Cell* 65:587–598; Benson et al. 1985 *Ann. Rev. Biochem.* 54:101–134). The signal peptide is often referred to in the literature as a "pre-peptide." A signal peptidase cleaves off the signal peptide during translocation within the endoplasmic reticulum. In the yeast *Saccharomyces cerevisiae*, the signal peptidase is the product of the SEC11 gene (Bohni, et al 1988 *J. Cell Biol.* 106:1035–1042).

For many secreted proteins, cleavage of the signal peptide results in production of the mature form of the protein. However, there are other secreted proteins, including, e.g., human insulin-like growth factor-I (IGF-I), that require, when they are to be secreted by yeast cells, a sequence between the carboxy-terminus of the signal peptide and the amino-terminus of the mature protein that is commonly known as a "pro" sequence. In the absence of a pro sequence some proteins are retained as intracellular, inactive precursors in the cell (Chaudhuri et al. 1992. *Eur. J. Biochem.* 206:793–800). The pro-protein (i.e., a protein precursor with an N-terminal pro sequence) remains intact during transport to the Golgi apparatus, but the pro sequence is subsequently removed in the trans-Golgi or secretory vesicles (Julius et al. 1984. *Cell* 36:309–318; Redding et al. 1991. *J. Cell Biol.* 113:527–538; Franzusoff et al. 1991. *J. Cell Biol.* 112:27–37). In *S. cerevisiae*, the pro sequence is removed by an endoproteinase (a product of the KEX2 gene) that is a trypsin-like protease and cleaves on the carboxyl side of a pair of dibasic amino acid residues (Julius et al. 1984. *Cell* 37:1075–1089).

In addition, several secreted proteins in yeast contain short spacer amino acid sequences preceding the N-terminus of the mature protein. For example, the lys-arg recognition sequence for the KEX2 protease also comprises part of a spacer sequence separating four repeats of the mature alpha-MF peptide in *S. cerevisiae*, and is cleaved initially by the KEX2 protease at the Arg-Glu peptide bond (Brake, 1990. *Meth. Enz.* 185:408–421). The remaining Glu/Asp-Ala repeats are removed subsequently by a membrane-bound dipeptidylaminopeptidase (Julius et al. 1983. *Cell* 32:839–852). The role the spacer sequences have in the secretion of endogenous or recombinant proteins is unclear.

SUMMARY OF THE INVENTION

The invention generally features a recombinant DNA molecule that includes the following DNA sequences joined in frame and in the following 5' to 3' progression: (a) a sequence encoding a signal peptide of a secreted protein; (b) a sequence encoding at least a 5 amino acid sequence of the N-terminal region of a mature yeast acid phosphatase protein; and (c) a sequence encoding a heterologous protein, wherein sequences (a) and (b) together, when positioned upstream from sequence (c) and under the control of a functional regulatory element, bring about secretion of the heterologous protein from a host yeast cell. The recombinant DNA molecule is preferably used to direct the secretion of a heterologous protein, preferably IGF-I, from a yeast cell using a novel secretion sequence.

A signal peptide can be any signal peptide which normally directs the secretion of a protein, preferably a secreted yeast protein. Preferably, a signal peptide is, without limitation, the 22 amino acid signal peptide of an acid phosphatase protein, although other signal peptides may be substituted, e.g., the human serum albumin (HSA) signal sequence, the signal peptide of yeast α-mating factor (α-MF), the invertase signal sequence, or the killer toxin signal sequence. Examples of an acid phosphatase gene include, but are not limited to, the acid phosphatase gene of *Pichia pastoris* (FIG. 3 and SEQ ID NO:25, amino acids 1–22; Eur. Patent Application 0 495 208 A2; hereby incorporated by reference), and either of the acid phosphatase genes of *Saccharomyces cerevisiae* (Meyhack et al. EMBO J. 6:675–680, 1982; hereby incorporated by reference). Additional yeast acid phosphatase genes will be known to those skilled in the art.

By "a sequence encoding at least a 5 amino acid sequence of the N-terminal region of a mature yeast acid phosphatase protein" (referred to herein as a Secretory Facilitating Element (SFE)) is meant a stretch of at least 5, or preferably at least 10, 15, 20, 30, or even 40 amino acids within the first 60 N-terminal amino acids of a naturally occurring mature yeast acid phosphatase protein. The SFE can be derived from a yeast acid phosphatase protein of any yeast species, e.g., a *S. cerevisiae* acid phosphatase protein (Meyhack et al. supra), but is preferably the *P. pastoris* acid phosphatase protein (EPA 0 495 208, supra; FIG. 3 and SEQ ID NO:26, amino acids 23–83).

Referring to both the signal peptide and the SFE, the present invention also provides for functional derivatives of a signal or SFE that differ from the corresponding naturally occurring amino acid sequence by sequence variations, e.g., substitutions, deletions, or modifications, that do not abolish the ability of the signal or SFE to direct the secretion of a heterologous protein, e.g., IGF-I. With respect to the signal, a functional derivative further includes a portion or fragment of the native signal of, e.g., 10, 15, or 20 amino acids, that retains the ability to direct secretion of the heterologous protein to which it is operably linked.

The ability of a candidate SFE or signal peptide to direct the secretion of biologically active protein from a host yeast cell can be readily determined by inserting the candidate SFE into a recombinant DNA molecule of the invention (the remaining elements of which have proven utility), and assaying for secretion of the heterologous protein, e.g., IGF-I, by the methods provided below. Detection of secretion of the heterologous protein while under the control of the candidate signal or SFE demonstrates that the candidate signal or SFE falls within the scope of the invention.

In a preferred embodiment, the recombinant DNA molecule further includes a DNA sequence (d) that encodes a cleavable processing site joined in frame and on the 3', or downstream, side of the sequence (b), and in frame and on the 5' side of the sequence (c). A "cleavable processing site", as used herein, is a sequence of amino acids that is recognized and cut by a sequence-specific proteolytic enzyme. A preferred cleavable processing site encoded by the DNA molecule is the amino acid sequence KR.

In another preferred embodiment, the recombinant DNA molecule further includes a DNA sequence (d) that encodes a spacer element, preferably joined in frame and on the 3' side of the sequence (b) and in frame and on the 5' side of the sequence (c). A "spacer element", as used herein, refers to a sequence of amino acids that includes a cleavable processing site plus 1 to 6 other amino acids that may enhance the efficiency of cleavage at the cleavable processing site. The sequences encoding a spacer element are such that one or more of the amino acids of the spacer are found on the 5' side of the cleavable processing site, and/or one or more amino acids of the spacer are found on the 3' sides of the cleavable processing site. The spacer element with its cleavable processing site is preferably at least two but less than ten amino acids in length (i.e., between 2 and 9 amino acids in length inclusive). Preferred examples of spacer elements encoded by the DNA molecule of the invention include EKR, EKRSLDKR (SEQ ID NO:24), or EKREA (SEQ ID NO: 43), most preferably EKREA.

In a most preferred embodiment, the invention features a recombinant DNA molecule that includes the following sequences joined in frame and in the following 5' to 3' progression: (a) a sequence encoding a signal peptide of a yeast acid phosphatase protein of Pichia; (b) a sequence encoding a 25 amino acid sequence of the N-terminal region of a mature yeast acid phosphatase protein of Pichia; (c) a sequence encoding a spacer element; and (d) a sequence encoding insulin-like growth factor-I (IGF-I), wherein sequences (a), (b), and (c) together, when positioned upstream from said sequence (d) and under the control of a functional regulatory element, bring about secretion of said IGF-I from a host yeast cell.

The proper positioning of DNA elements encoding a signal peptide, an SFE, and a cleavable processing site within a spacer element (collectively referred to as "secretion sequences") are illustrated in FIG. 1 between a transcriptional promoter in the 5' direction and a heterologous protein encoding sequence in the 3' direction.

The host cell can be any yeast cell, known to one skilled in the art, in which a signal encoded by a yeast acid phosphatase gene is biologically active. Preferably the host cell is *Pichia Pastoris* (*P. pastoris*). The recombinant DNA molecule can be incorporated into the cell on an autonomously replicating episomal plasmid, such as one derived from the multi-copy 2 micron or pKD1 plasmids (U.S. Pat. No. 5,166,070). Preferably, however, the DNA is integrated into the chromosome of the host cell in one or more copies. For example, the recombinant DNA molecule can be incorporated into the chromosome in the form of an expression cassette comprising from 1 to 10, preferably 4, or most preferably 6, copies of any of the various recombinant molecules described above. The recombinant DNA molecule is introduced to the host cell by a method, e.g., by transformation or transfection, known to one skilled in the art.

A cell, i.e., either a eukaryotic cell or a prokaryotic cell, containing any of the various recombinant DNA molecules provided herein, is within the scope of the invention. Where the cell is a prokaryotic cell, e.g., an *E. coli* cell, it is useful for maintaining or propagating copies of a recombinant DNA molecule of the invention to which it is host. Where the DNA is a eukaryotic cell, preferably a yeast cell, more preferably *P. pastoris*, it is useful not only for maintenance and propagation of the recombinant DNA molecule, but also for expression and secretion of the protein, e.g., IGF-I, being produced. A yeast cell, e.g., *P. pastoris*, within the scope of the invention is preferably transformed with multiple copies of a recombinant DNA of the invention. Preferably, 1 to 10, most preferably 4 to 6, copies of a recombinant DNA of the invention are integrated into the chromosome of the cell.

A protein expressed from any of the various recombinant DNA molecules that are taught and claimed herein is included within the scope of the invention.

The invention also features a method of producing a heterologous protein, preferably IGF-I. The method involves the steps of: (a) providing any of the various recombinant DNA molecules of the invention in a host yeast cell; e.g, the DNA molecule including the following sequences joined in frame and in the following 5' to 3' progression: (i) a sequence encoding a signal peptide of a secreted protein; (ii) a sequence encoding at least a 5 amino acid sequence of the N-terminal region of a mature yeast acid phosphatase protein; and (iii) a sequence encoding a heterologous protein, wherein sequences (i) and (ii) together, when positioned upstream from sequence (iii) under the control of a functional regulatory element, bring about secretion of the protein from the host cell; and (b) isolating the heterologous protein being produced from the extracellular medium of the host cell. In a preferred embodiment, the recombinant DNA molecule used in a method of the invention further includes a DNA sequence (iv) that encodes a cleavable processing site joined in frame and 3' to the sequence (ii). In another preferred embodiment, the recombinant DNA molecule used in a method of the invention further includes a DNA sequence (iv) that encodes a spacer element, preferably joined in frame and on the 3' side of the sequence (ii) and in frame and on the 5' side of the sequence (iii). A cleavable processing site is found within the spacer element.

The invention also includes a protein produced by any of the various methods of the invention.

The following terms are used herein as follows. An "upstream" DNA sequence is one that is either in the 5' direction of, or that is transcribed previously to when contiguous with, the heterologous protein coding sequence. A "downstream" DNA sequence is one that is either in the 3' direction of, or is transcribed subsequently to when contiguous with, the heterologous protein coding sequence. By a "functional regulatory element" is meant a DNA sequence that affects transcription of a protein coding sequence under its control, e.g., a promoter sequence. The coding sequence is preferably operably linked to the functional regulatory element, i.e., is sufficiently proximal to the promoter for an RNA transcript initiated at the promoter to include messenger RNA that is complementary to that coding sequence. The "promoter" region is a segment of DNA 5' to the transcription start site of a gene or other polypeptide encoding segment of DNA, to which RNA polymerase binds before initiating transcription of the gene or coding segment. By "in frame" is meant that two coding sequences, e.g., two contiguous coding sequences, are translated in the same translational reading frame. By "joined in frame" is meant that the ribosomal translation apparatus can accurately read the triplet code continuously from one protein-encoding region to the next. A "recombinant DNA molecule" is a DNA molecule that results from cleavage and ligation of DNA from at least two different sources, e.g., from two different regions of the DNA of an organism, or from two different organisms. A protein or nucleic acid is considered to be "homologous" if it is naturally occurring in the host yeast strain employed to express and secrete the protein being produced. A protein or nucleic acid is considered to be "heterologous" if it is not naturally occurring in the host yeast strain employed to express and secrete the protein being produced. By "secrete" is meant the transport of a protein into or through the plasma membrane of a cell. By "secreted yeast protein" is meant a protein that, in its naturally occurring state, is transported into or through the extracellular membrane of its native cell.

Other features and advantages of the invention will be apparent from the following description of the preferred embodiments thereof, and from the claims.

DETAILED DESCRIPTION

The drawings will first be described.

FIG. 3 shows the nucleotide and amino acid sequences of the recombinant templates PSS (SEQ ID NO:25), PPI (SEQ ID NO:26), PKV (SEQ ID NO:27), PKD (SEQ ID NO:28), AM5 (SEQ ID NO:29), PPSI (SEQ ID NO:30), PPEAI (SEQ ID NO:31), INV (SEQ ID NO:32), INVS (SEQ ID NO:33), and HSA (SEQ ID NO:34). The signal, SFE, pro, and spacer sequences are labelled below each corresponding sequence.

FIG. 6 is a diagrammatic representation of the 2-template reaction strategy for polymerase chain reaction (PCR) construction of signal/IGF-I recombinant DNA templates.

Figure 8:
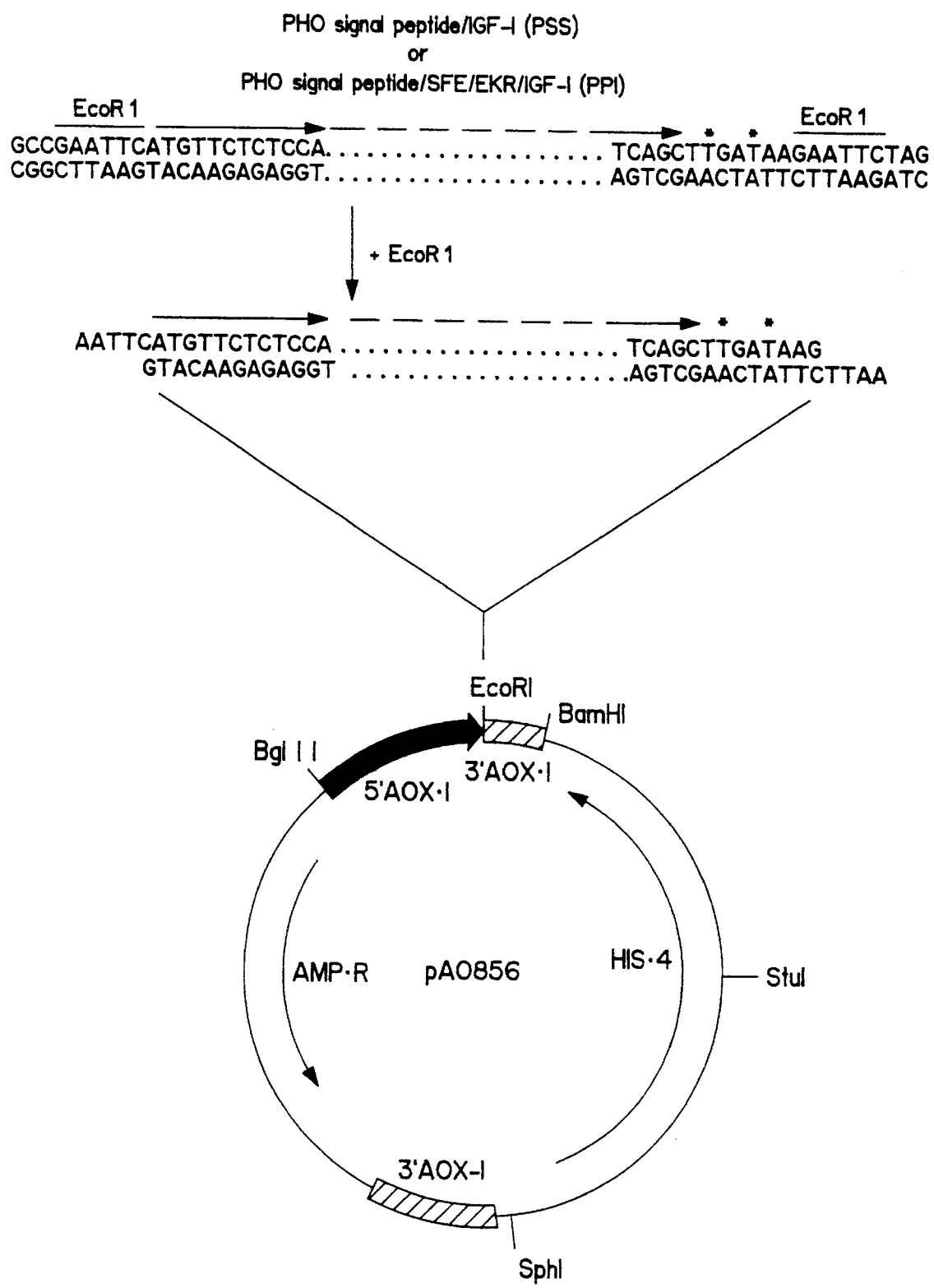
FIG. 8 is a diagrammatic representation of the assembly of the PSS and PPI expression vectors in pAO856.
Figure 9A:
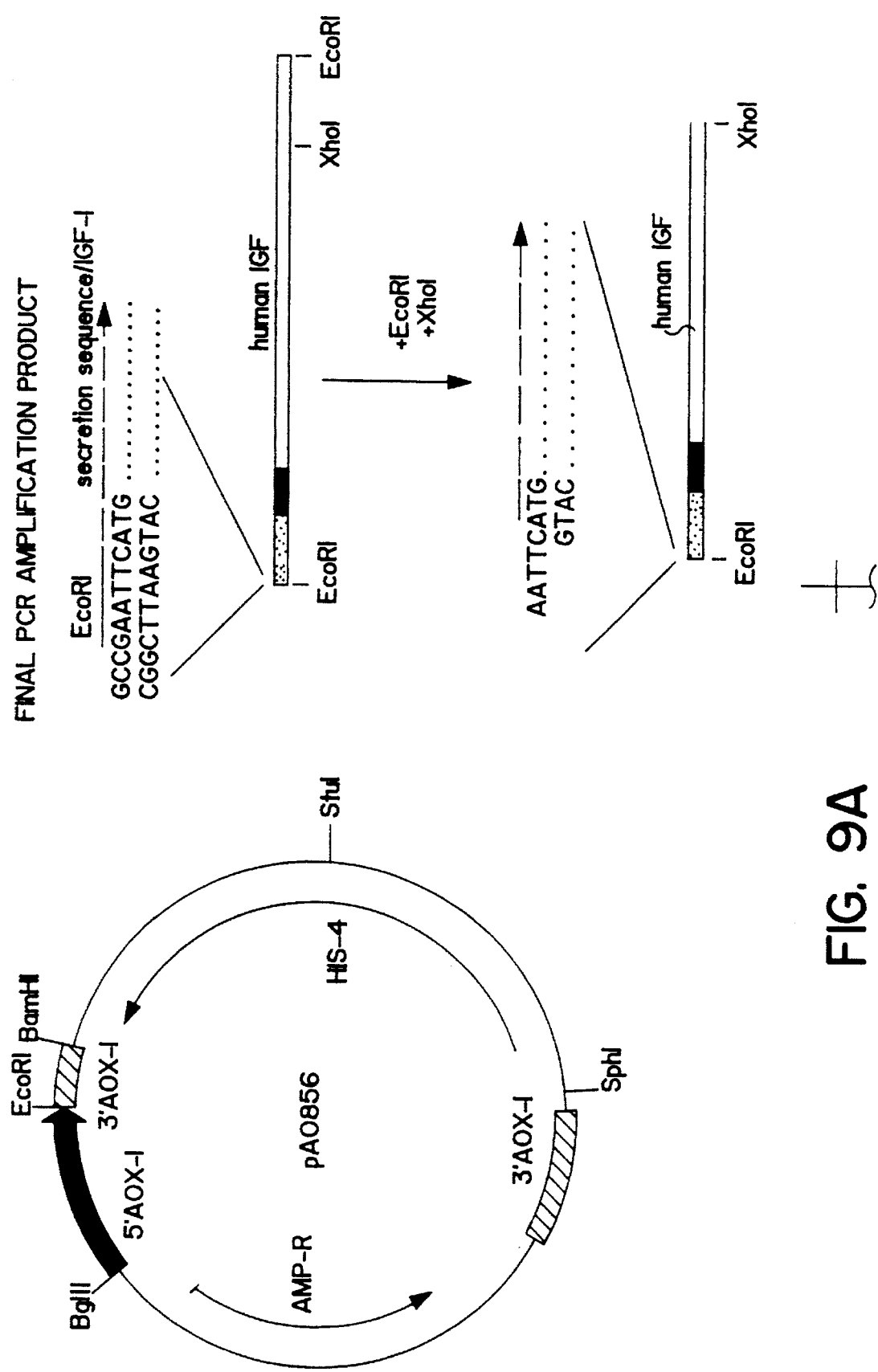
Figure 9B:
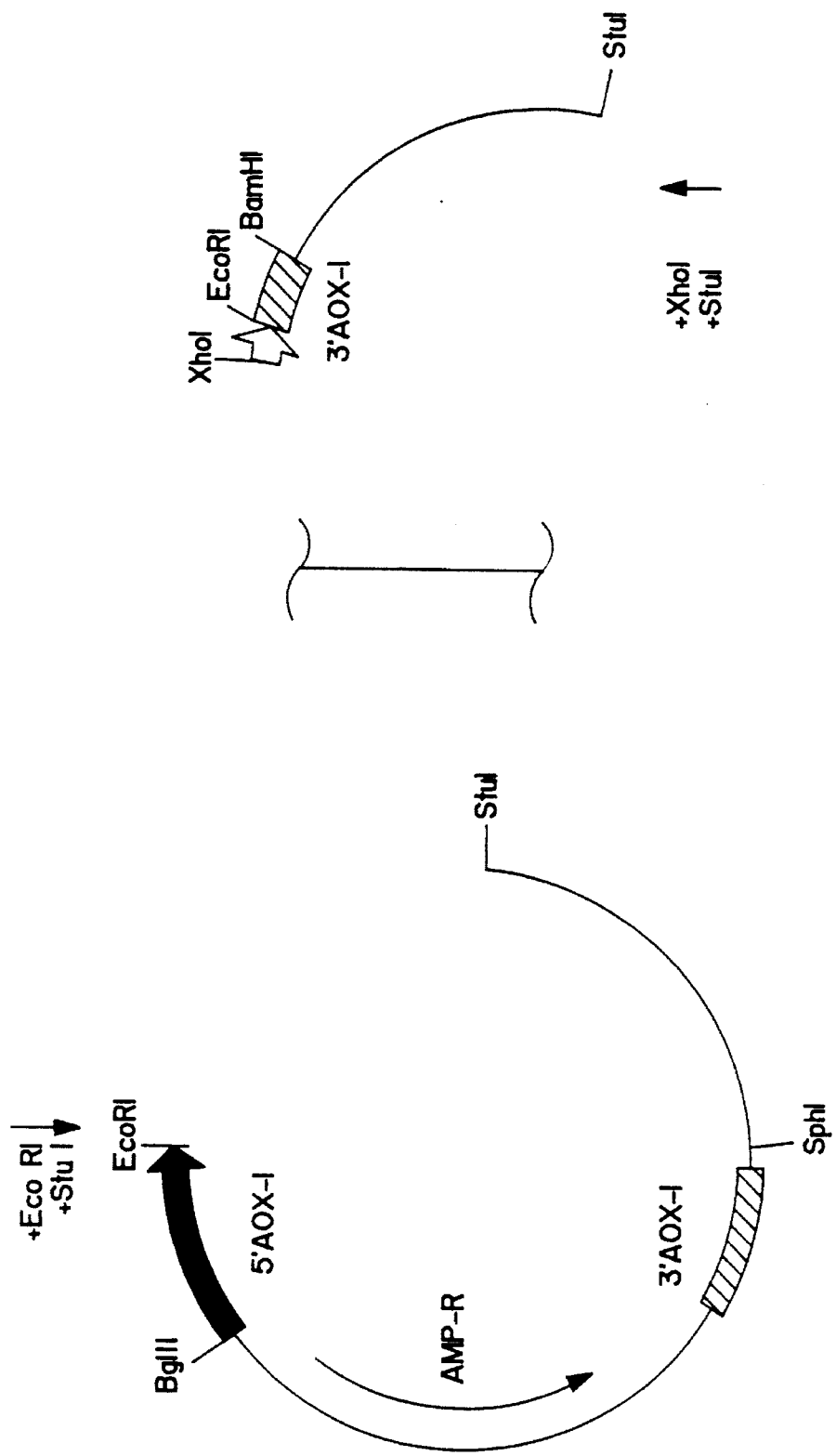
Figure 9C:
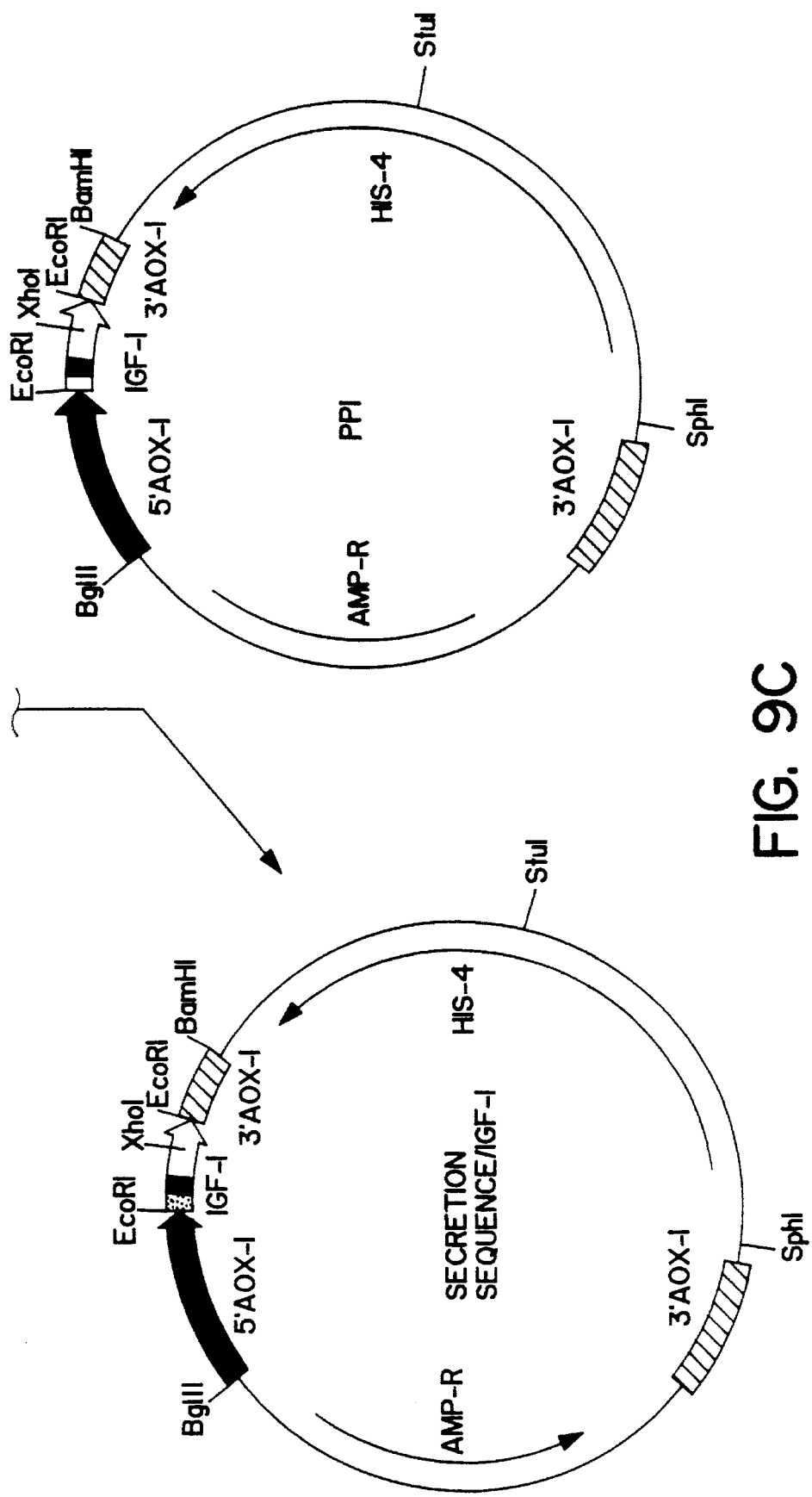

FIG. 9 is a diagrammatic representation for the assembly of various expression vectors into the PPI/pAO856 construct of FIG. 8. The sequence "GCCGAATTCATG" corresponds to nucleotide 1–12 of SEQ ID N0:35. The sequence "CGGCTTAAGTAC" corresponds to nucleotide 1–12 of SEQ ID N0:37. The sequence "AATTCATG" corresponds to nucleotide 5–12 of SEQ ID NO:35.

Figure 10A:
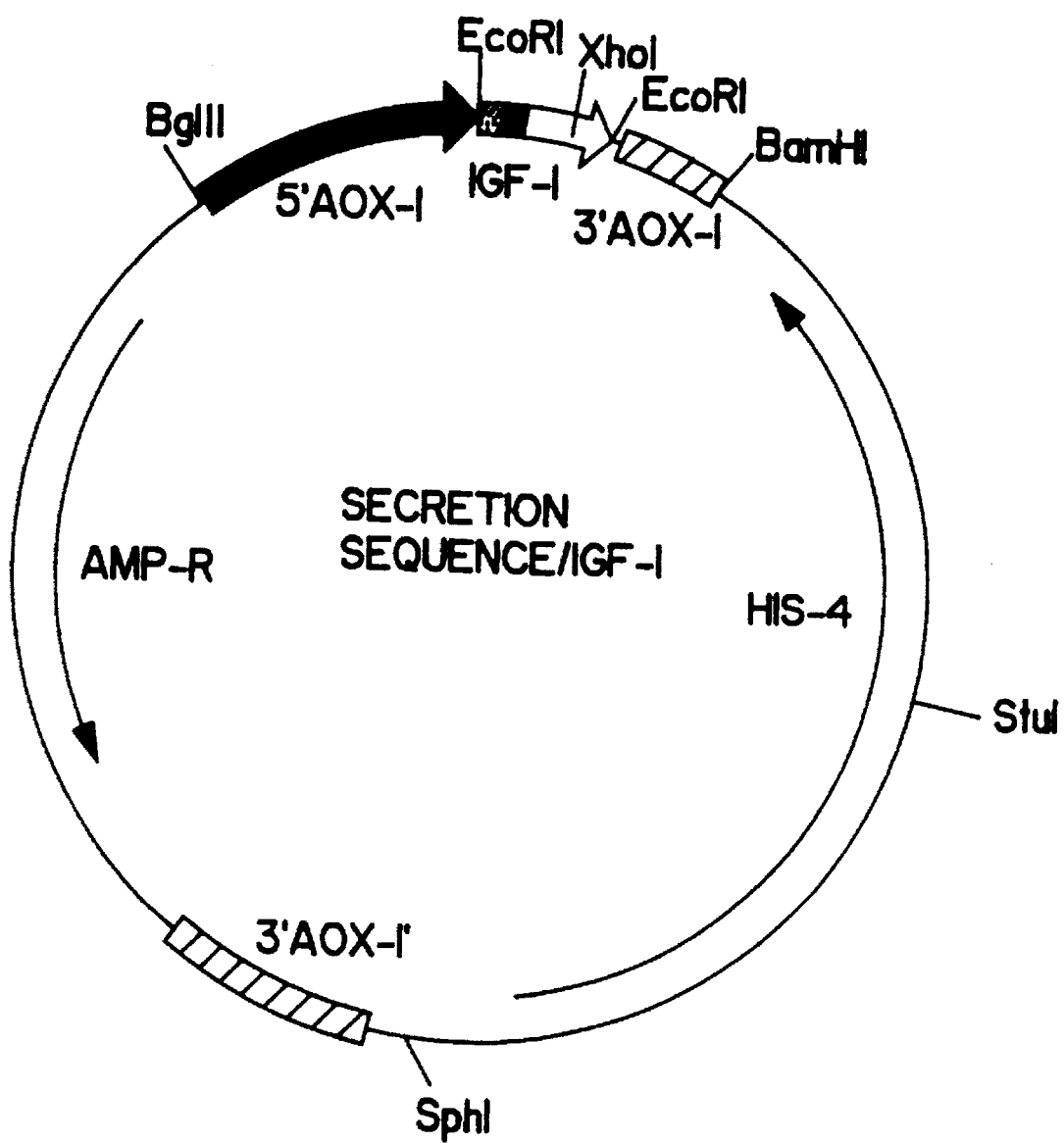
Figure 10B:
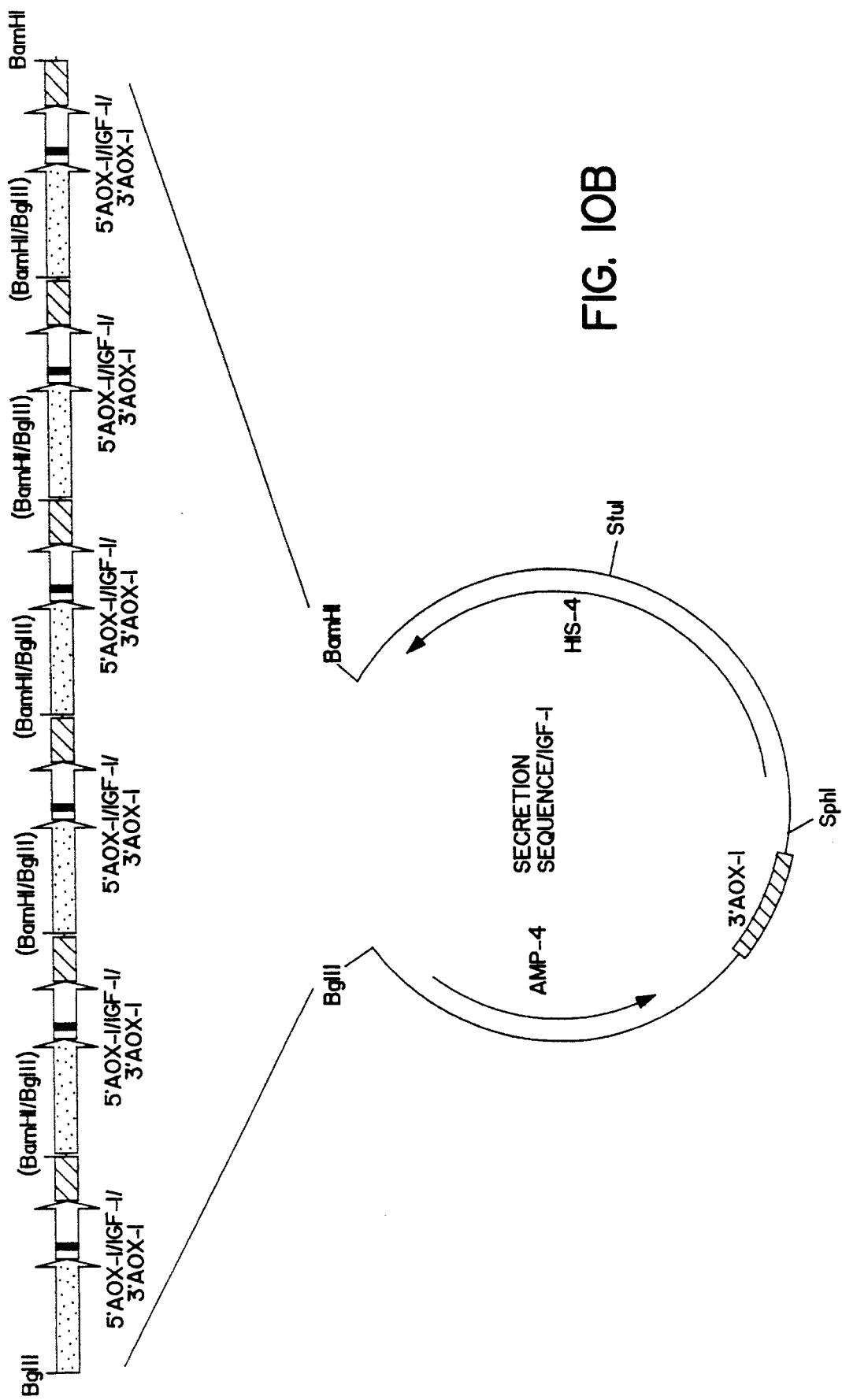

FIG. 10 shows two circular maps of the single-copy and six-copy IGF-I expression vectors, respectively.

Figure 11:
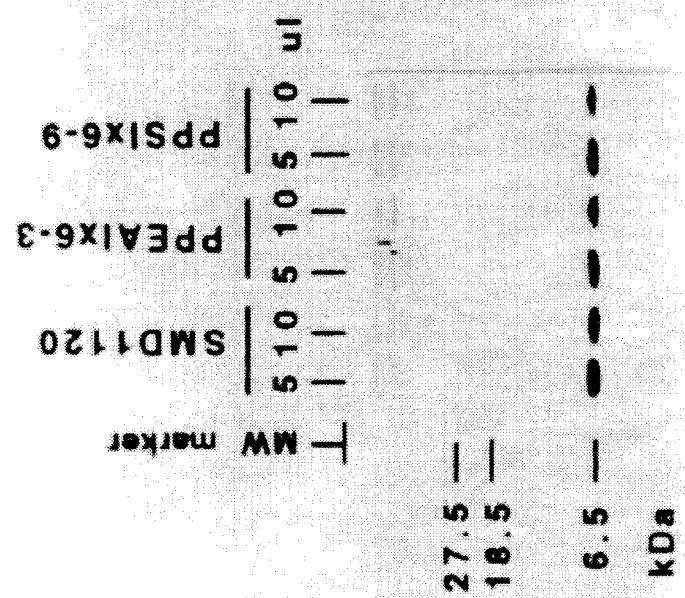

FIG. 11 shows an immunoblot assay of conditioned culture broth samples from P. pastoris transformants SMD1120, PPEAIx6, and PPSIx6.

IGF-I is a single-chain, 70 amino acid protein that requires the formation of three intracellular disulfide linkages for biological activity. In mammals, IGF-I is found in serum and cerebrospinal fluid. IGF-I affects a number of biological responses including cell replication and growth (LeRoith et al. 1992 In: Pancreatic Islet Cell Regeneration and Growth, Vinik, ed. A. I. Plenum Press, N.Y., pg. 21–30), neurite outgrowth, and survival of neuronal populations in the peripheral and central nervous systems (Lauterio, 1992 In: Pancreatic Islet Cell Regeneration and Growth, Vinik, Ed. A. I. Plenum Press, N.Y. pg. 31–36), including populations of spinal cord motor neurons.

High level expression and secretion of biologically active IGF-I is a particularly challenging goal for a recombinant protein expression system. Correct intracellular passage of IGF-I through the endoplasmic reticulum, the Golgi complex and secretory vesicles is necessary to achieve efficient secretion, protein folding, and resistance to proteolytic degradation. Yeast are ideal for producing IGF-I because they provide a proper oxidative/reductive environment that is suitable for disulfide bond formation and for secretion of properly folded protein. The yeast environment also provides a good back-drop for scale-up of the cellular production machinery and culture conditions.

It is thus a general object of the present invention to provide an expression system in a yeast host that is capable of directing the secretion of a heterologous protein. In particular, it was applicants' goal to design a DNA construct to be used for expressing and secreting IGF-I in the methylotrophic yeast strain P. pastoris.

The success of the resulting construct was demonstrated by making a number of comparative expression systems and screening for their ability to direct efficient secretion of IGF-I from P. pastoris. In so doing, applicants discovered that a sequence from the N-terminal region of the mature P. pastoris acid phosphatase gene, in combination with signal and cleavable spacer sequences, was most effective at directing the expression of a high amount of biologically active IGF-I.

Rational for the Design of a DNA Construct for the Expression and Secretion of IGF-I In order to design an expression/secretion system to optimize the production of IGF-I each element was chosen with the considerations described below. A diagram of the resulting recombinant DNA constructs, each with different signal peptide, SFE, and spacer element combinations, appears in FIG. 2. The nucleotide sequence and corresponding amino acid sequence for each template are shown in FIG. 3.

Host cells: Use of methylotrophic yeast cells such as P. pastoris offers several advantages for the expression of a heterologous protein (Cregg, J. M. et al. 1989. In: Genetics and Molecular Biology of Industrial Microorganisms. Hershberger et al. Eds., Amer. Soc. Microbiology, pg. 343–352). First, strong and tightly regulated promoters, necessary for efficient and well-controlled expression of recombinant proteins, have been isolated from P. pastoris. Second, glycosylation of recombinant proteins during passage through the secretory pathway in P. pastoris is not as extensive as the hyperglycosylation that occurs in S. cerevisiae (Grinna et al., 1989. Yeast 5:107–115; Trimble et al. 1991. J. Biol. Chem. 266:22807–22817) and this may account for the high efficiency of recombinant protein secretion by P. pastoris relative to S. cerevisiae (Buckholz et al., 1991; Biotechnology 9:1067–1072). Third, *P. pastoris* yeast cells can be grown to high cell densities to maximize production and recovery of secreted proteins. Fourth, the culture conditions for growing the cells are well characterized and easily adaptable to shake flask or fermentor cultures.

Other yeast strains in which the preferred signal/SFE/ spacer construct would be operable are: *Saccharomyces sp., Kluveromyces sp., Yerwinia sp.,* and *Hansenula sp.*

Protein Expression and Functional Regulatory Elements: All expression systems were under the control of the *P. pastoris* alcohol oxidase I (AOX-I) promoter (Cregg et al. 1989. *Mol. Cell. Biol.* 9:1316–1323). The AOX-I promoter is advantageous for constructing an efficient expression system. The AOX-I promoter is 1) capable of high level expression, 2) maintained in a mode that is silent with respect to transcription during scale-up of the cultures, thereby avoiding undo selective pressure against growth of the recombinant cells, and 3) economically induced by the addition of methanol to the culture broth. A protocol for the induction of the methanol-inducible AOX-I promoter is provided below.

Additional promoters useful for expressing the recombinant DNA molecules herein include, but are not limited to, the alcohol oxidase 2 (AOX-2) promoter, the alcohol dehydrogenase (ADH) promoter, and the phosphoglycerol kinase (PGK) promoter.

Figure 4:
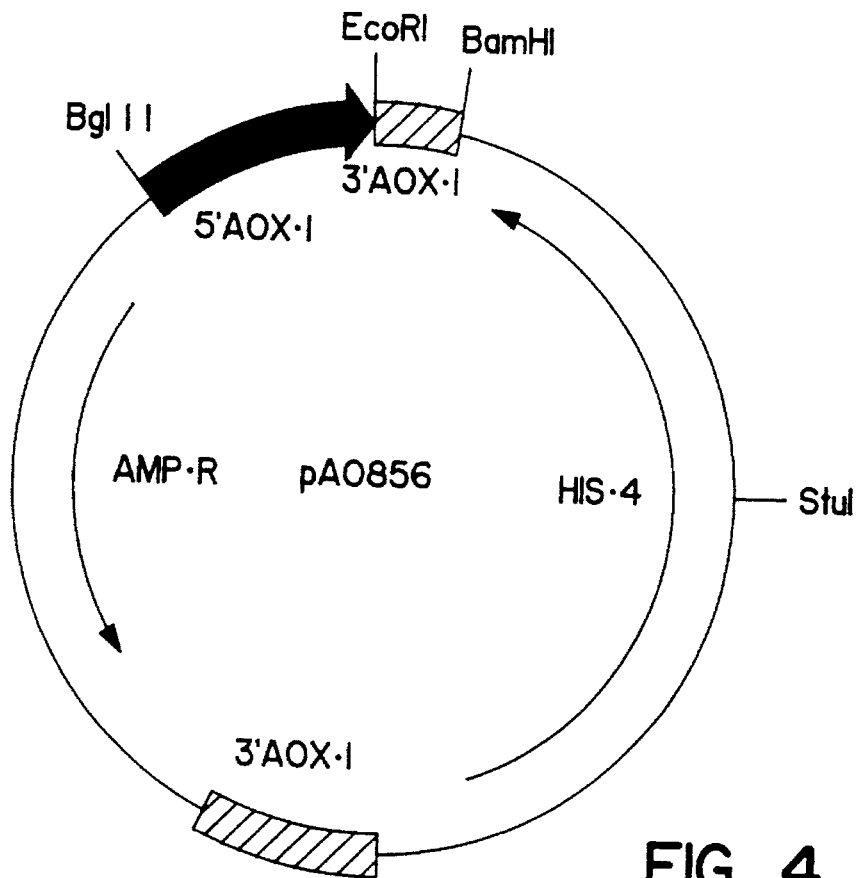
FIG. 4 is a circular map of the pAO856 expression vector.

The expression vector used as a basis for constructing the recombinant templates provided herein is pAO856 (WO 92/13951; FIG. 4). In addition to DNA sequences required for efficient propagation in bacteria and yeast, the pAO856 vector carries the AOX-I methanol-inducible promoter and the AOX-I transcription terminator, the latter being required for proper RNA processing. Additional DNA sequences, e.g., protein coding sequences, can be operably linked to the AOX-I regulatory elements by inserting them at the unique EcoR1 restriction site (at nucleotide 7709 of pAO856; FIG. 4 and W092/13951). A HIS4 marker gene on pAO856 is useful for selecting DNA transformants by histidine auxotrophy. The HIS4 or AOX-I plasmid sequences are also useful for direct integration of the vector into the host genome, since the plasmid sequences help to target recombination at the sites of the genomic HIS4 or AOX-I loci, respectively.

Secreted proteins are sometimes susceptible to proteolytic degradation which would result in reduced protein yields. Culture conditions can be altered by adjusting the pH so as to inactivate certain extracellular proteases, while taking care not to adversely affect the growth of the host organism, or to affect production and stability of the recombinant protein (Clare et al. 1991. *Gene* 105:205–212; EPA 0510678A2, both hereby incorporated by reference). Modifications can also be made to the host organism to decrease its production of proteolytic enzymes. This approach has been taken successfully in *E. coli* (U.S. Pat. No. 4,758,512) and yeast (Jones et al. 1990. *Meth. Enz.* 185:372–386; IPN WO 92/17595).

Signal Peptide: Sequences encoding various signal peptides were derived from several sources. Templates PSS, PPI, PKV, PKD, AM5, PPSI, and PPEAI each contain the 22 amino acid PHO signal sequence of the *P. pastoris* acid phosphatase gene (EPA 0 495 208 A2). Templates INV and INVS contain the *S. Cerevisiae* invertase signal sequence (Carlson et al. 1983. *Mol. Cell. Bio.* 3:439–447). Template HSA contains the human serum albumin signal sequence (Sleep et al., 1990. *Biotechnology*, 8:42–46).

SFE: In agreement with published information, a pro sequence, in addition to the signal sequence, was found to be necessary for IGF-I secretion. However, applicants found that an efficacious sequence for performing this "pro-like" function was not a pro sequence at all, but rather was a 25 amino acid portion of the mature acid phosphatase protein of *P. pastoris*. This region, dubbed an SFE, was fused downstream of the acid phosphatase signal, and upstream and in-frame with the sequence encoding IGF-I (templates PPI, PPSI, and PPEAI).

In order to compare the advantages of different designs of secretion constructs, various templates were prepared that had different alternative SFE or pro sequences. Examples included the pro sequence of the yeast *Kluyveromyces lactis* killer toxin protein (Sleep et al., supra) (templates PKV and PKD); and the HSA pro sequence (Sleep et al., supra) (template HSA). (PKD is identical to PKV except that it contains a V to D substitution in the killer toxin pro sequence (FIG. 3)).

Other comparative templates that included neither the SFE nor a pro sequence included PSS, AM5, INV, and INVS.

As shown herein, a combination which gave high yields of IGF-I was discovered to be a sequence constructed from the *P. pastoris* acid phosphatase signal and the acid phosphatase SFE. To construct a recombinant molecule containing this sequence, the 25 amino acid N-terminal portion of the mature acid phosphatase protein can be fused downstream of the acid phosphatase signal peptide and upstream and in frame with the sequence encoding IGF-I. The use of the N-terminal 25 amino acids is provided as an example herein, and is not intended to limit the invention. A PHO SFE can include any sequence of amino acids from within the N-terminal portion of the acid phosphatase sequence, e.g., a segment of at least 5 amino acids from the N-terminal 60 amino acids of yeast acid phosphatase, that is shown empirically to successfully direct the secretion and folding of IGF-I by the methods provided herein.

Spacer Sequence: In order to liberate mature IGF-I from constructs containing an SFE, a DNA sequence encoding a spacer element (EKR) that contains a cleavable lys-arg processing site was inserted downstream of the SFE and upstream of the sequence encoding IGF-I (template PPI, FIG. 2). This allowed for cleavage and removal of the SFE by the KEX2-like secretory processing protease, which recognizes the KR site. The acidic residue glutamic acid (E) was included in one spacer element to provide a favorable context for cleavage (Zsebo et al., J. Biol. Chem. 261:5858–5865, 1986). Another DNA sequence is that encoding SLDKR (SEQ ID NO: 44) where SLD replaces E of the previous spacer sequence. In another DNA sequence, EKR was increased in length by adding nucleotides which encoded amino acid residues SLDKR (SEQ ID NO: 44) which contains the additional cleavage site KR and in still another DNA sequence, the amino acids EA were added to the EKR spacer element. Examples of the resulting lengthened spacer elements included EKRSLDKR (SEQ ID NO. 24) (template PPSI), EKREA (SEQ ID NO: 43) (template PPEAI). The pro peptide SLDKR (SEQ ID NO: 44) (templates AM5 and INVS) also included the cleavable processing site KR and could function as a spacer element in other constructions.

The templates PSS, PKV, AM5, INV, INVS and HSA did not contain spacer sequences. In these templates, the sequences preceding the sequence of the protein to be expressed (either a signal or pro sequence) included their own cleavage sites. They were therefore fused directly in frame with the IGF-I coding sequence.

The effectiveness of the spacer sequences was tested by measuring the yields of fully-processed, mature secreted IGF-I produced by transformants containing templates with the spacers. These levels were compared to yields from corresponding transformants lacking spacer sequences.

Other candidate spacer elements generally include an acidic amino acid residue followed by two dibasic amino acid residues, and will be known to those skilled in the art. Some examples include, but are not limited to, the amino acid sequences RR, RK, and PR.

Figure 1:
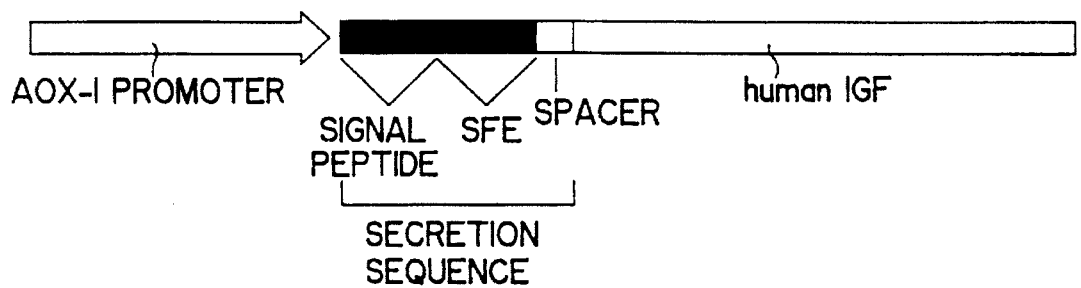
FIG. 1 is a diagram defining the positional relationship 5' to 3' between a promoter, signal peptide, SFE, spacer elements, and a heterologous protein, e.g., human IGF.
Figure 2A:
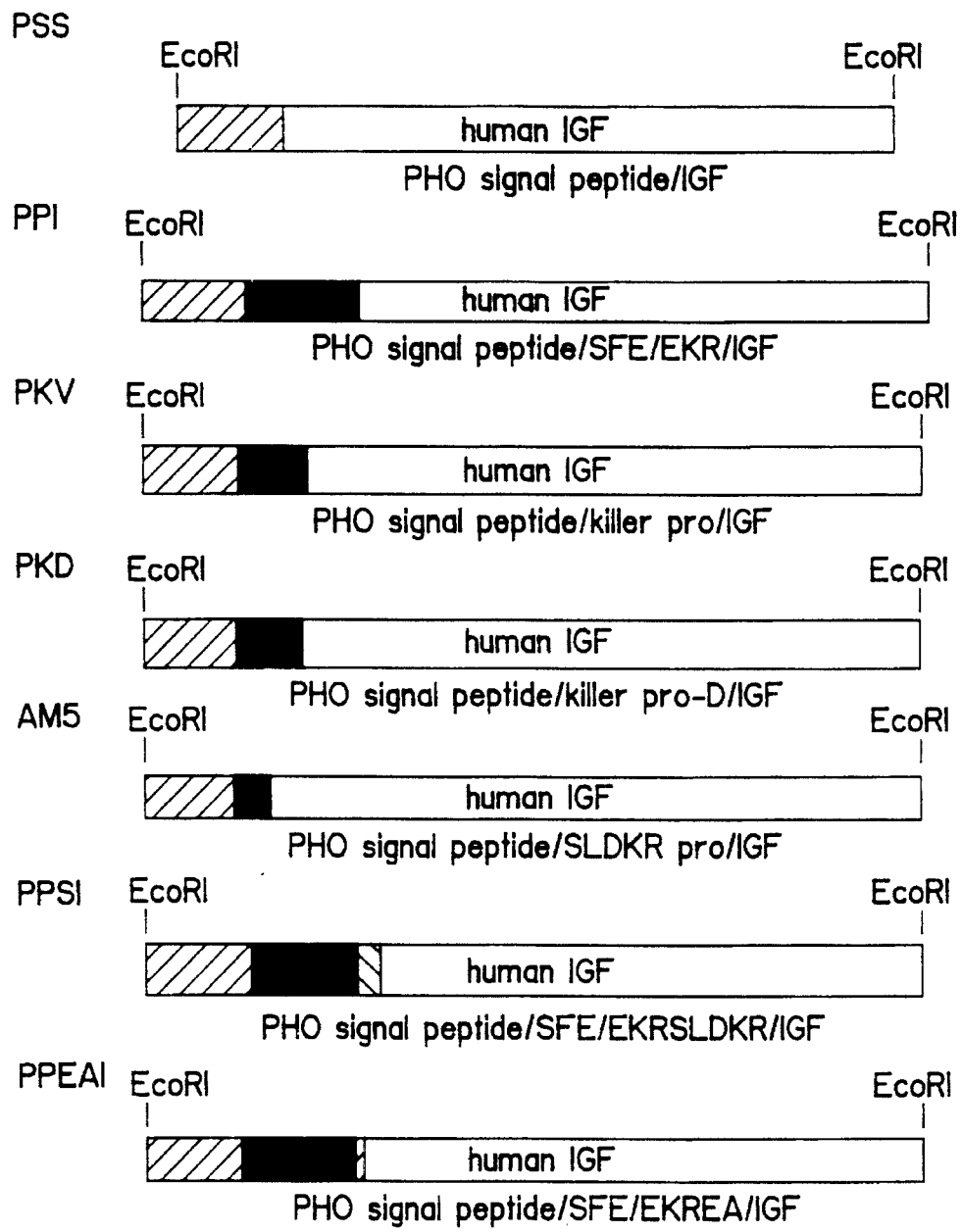
FIG. 2 is a diagram of recombinant DNA molecules that include a secretion sequence and a sequence encoding IGF-I. The recombinant templates are PSS, PPI, PKV, PKD, AM5, PPSI, PPEAI, INV, INVS, and HSA.
Figure 2B:
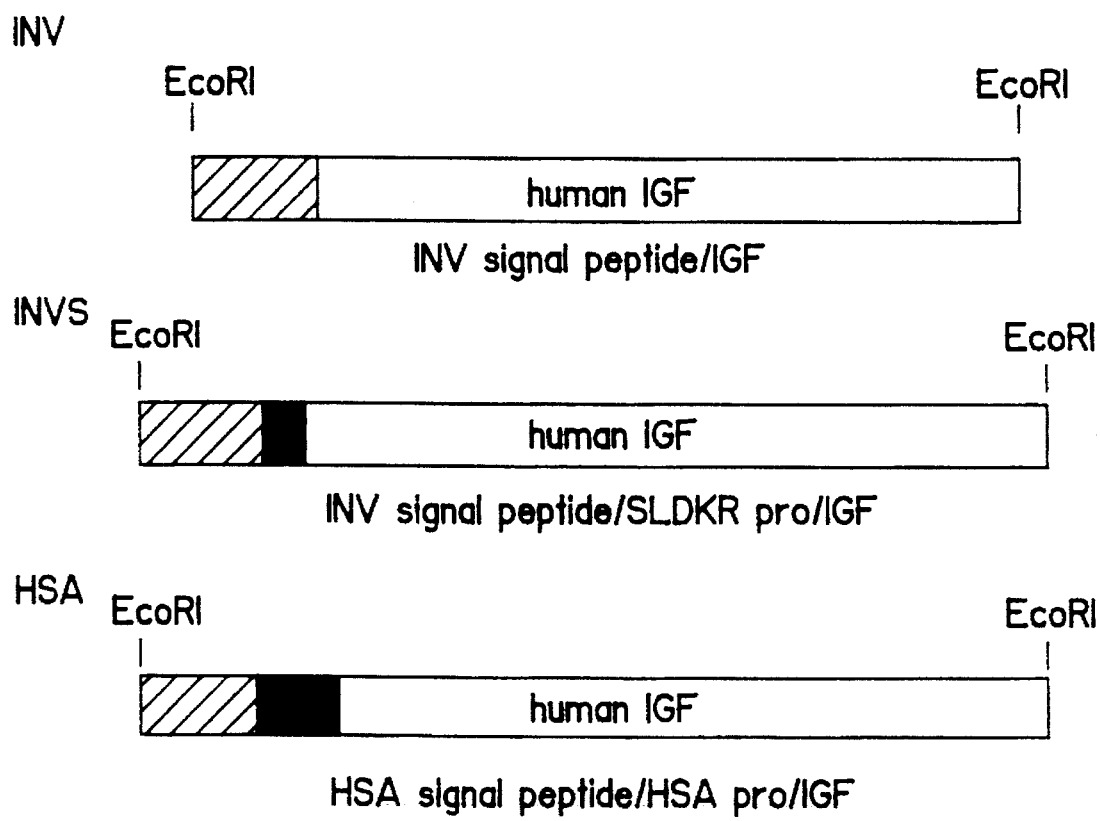

The spacer sequences for each template are shown in FIGS. 2 and 3.

Figure 5:
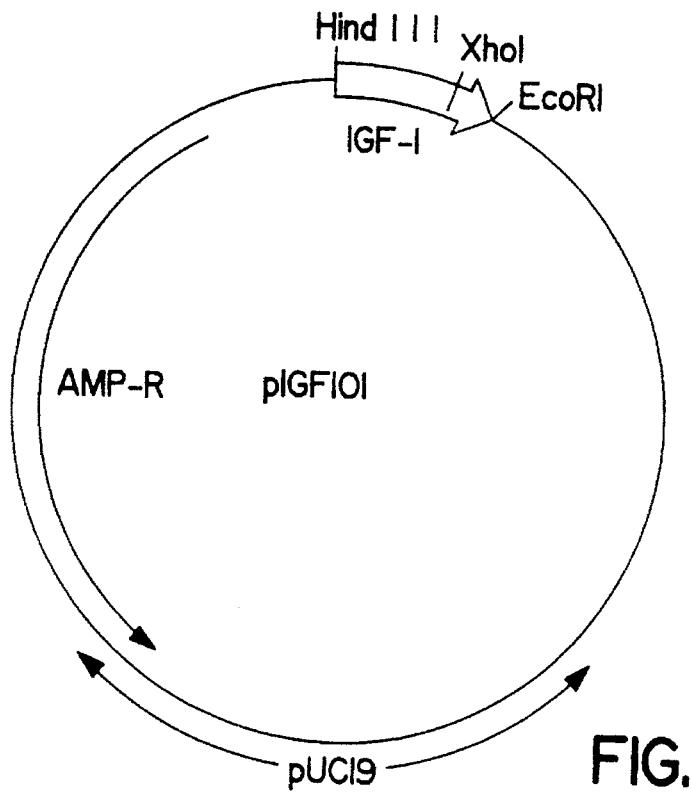
FIG. 5 is a circular map of the pIGF101 plasmid.

Protein Coding Sequences: The IGF-I coding sequences were derived by PCR amplification (Ho et al. 1989. *Gene* 77:51–59, hereby incorporated by reference) of pIGF101, a pUC9-based cloning vector containing the gene coding for mature human IGF-I (WO 92/04363 FIG. 5). Genes encoding other proteins of the IGF family, e.g., IGF-II, IGF-III, or des (1–3) IGF-I, can be substituted for the IGF-I sequences used herein. In addition, other non-IGF protein coding sequences can be expressed using the same expression system provided herein by substituting the IGF-I coding sequences with the alternative gene of interest. Candidate proteins, their corresponding genes, and motivation for their expression are known to those skilled in the art.

Example 1

Methods for Construction of Recombinant DNA Templates

General PCR strategy for constructing recombinant templates: Recombinant templates were constructed using an overlap PCR extension method (Ho et al. 1989. supra). The general reaction protocol was as follows:

The PCR reactions were done in 10 mM Tris-HCl, pH 9.0, 50 mM KCl, 0.1% Tritonx100 ™, 2 mM $MgCl_2$, 0.2 mM each of dATP, dCTP, dGTP and dTTP, 1 μM each of the oligonucleotide primers, 10 ng of DNA template, and 1 unit of TL1 DNA polymerase (Promega Biotec). The PCR cycles were 1 cycle at 95° C. for 5 minutes, 35 cycles of 1 minute at 95° C. and 1 minute at 60° C., 1 cycle at 60° C. for 7 minutes, and a 4° C. soak cycle at the conclusion of the reaction. The final amplified products were resolved by agarose gel electrophoresis, excised, and eluted with the Gene-Clean reagent according to the directions of the vendor (Bio 101, Inc.).

Figure 7:
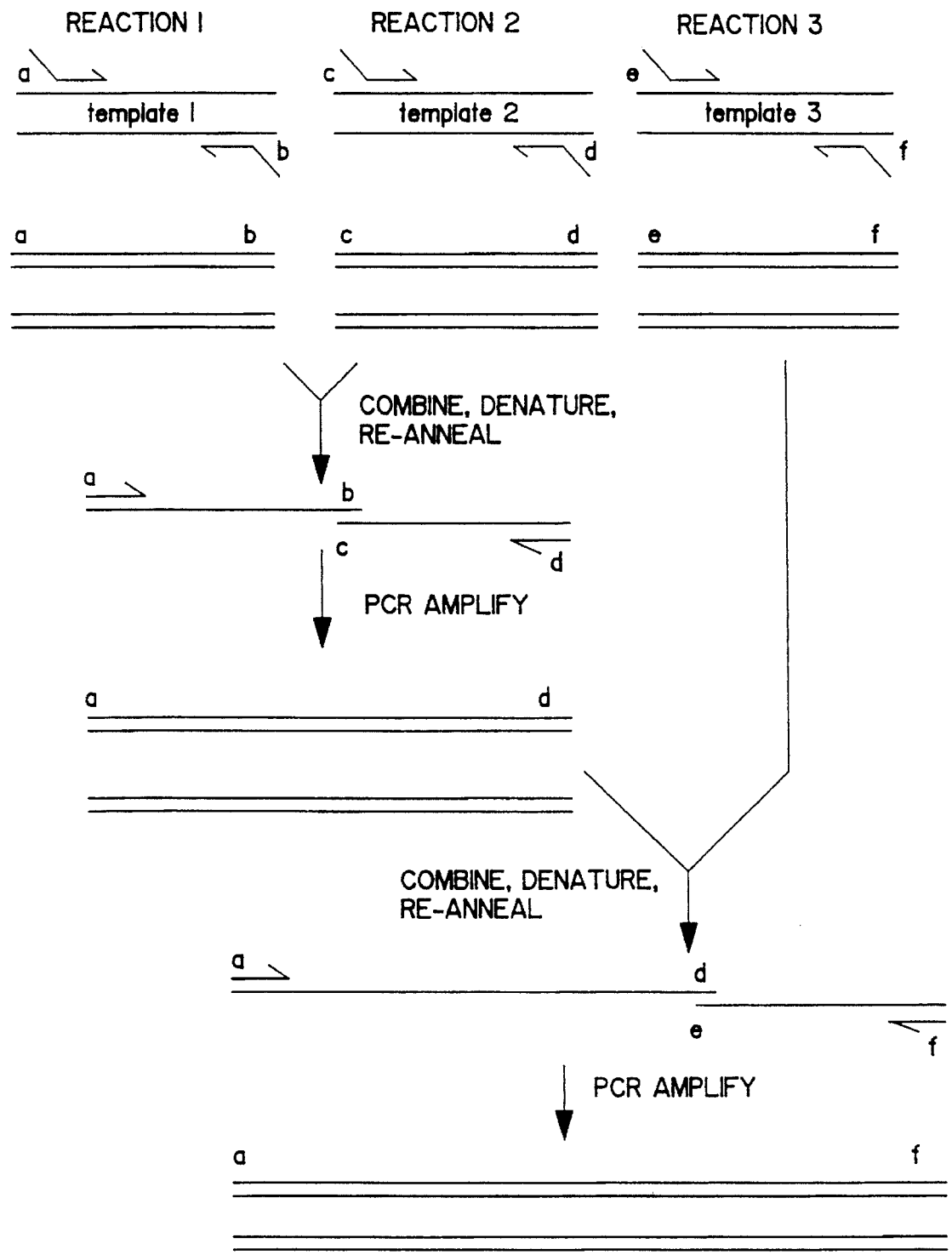
FIG. 7 is a diagrammatic representation of the 3-template reaction strategy for PCR construction of the signal/SFE/IGF-I recombinant DNA template PPI.

Either a two template strategy or a three template strategy was used, depending on the number of templates required to synthesize the recombinant template. These strategies are outlined in FIGS. 6 and 7, and the oligonucleotide primers used in the amplification reactions for the construction of each template are listed in Table 1.

TABLE 1

Recombinant DNA Constructs Templates and Primers for PCR Reactions

PSS (2 template PCR reaction)
   Template 1 = pHILS1 (SIBIA; plasmid DNA containing the *P. pastoris* acid phosphatase (PHO) signal sequence)
   Template 2 = pIGF101 (SIBIA; plasmid DNA containing the human IGF-I coding sequence)
Primer a= PSS-1:5'dGCCGAATTCATGTTCTCTCCAATTTTCTCCTTG 3'(SEQ ID NO: 1)
Primer b= PSS-2:5'dGAGCGTCTCCGGTCCAGCGAAGACAGATTGCAA 3'(SEQ ID NO: 2)
Primer c= PSS-3:5'dCAATCTGTCTTCGCTGGACCGGAGACGCTCTGC 3'(SEQ ID NO: 3)
Primer d= PSS-4:5'dCTAGAATTCTTATCAAGCTGACTTGGCAGGCTTGA 3'(SEQ ID NO: 4)
PPI (3 template PCR reaction)
   Template 1 = pHILS1
   Template 2 = *P. pastoris* genomic DNA
   Template 3 = pIGF101
Primer a= PSS-1:5'dGCCGAATTCATGTTCTCTCCAATTTTCTCCTTG 3'(SEQ ID NO: 1)
Primer b= PPI-1:5'dGTGCTGCAACTCAACAGCGAAGACAGATTGCAA 3'(SEQ ID NO: 5)
Primer c= PPI-2:5'dCAATCTGTCTTCGCTGTTGAGTTGCAGCACGTT 3'(SEQ ID NO: 6)
Primer d= PPI-3:5'dGAGCGTCTCCGGTCCACGCTTCTCCAGAATGTTGT ACTG 3' (SEQ ID NO: 7)
Primer e= PPI-4:5'dATTCTGGAGAAGCGTGGACCGGAGACGCTCTGC 3'(SEQ ID NO: 8)
Primer f= PSS-4:5'dCTAGAATTCTTATCAAGCTGACTTGGCAGGCTTGA 3'(SEQ ID NO: 4)
PKV (2 template PCR reaction)
   Template 1 = pHILS1
   Template 2 = pIGF101
Primer a= PSS-1:5'dGCCGAATTCATGTTCTCTCCAATTTTCTCCTTG 3'(SEQ ID NO: 1)
Primer b= KT-1:5'dGGAGCCTCTTCGATGAGTATGCTCCAAAGCGAAGACAGA TTGCAA 3' (SEQ ID NO: 9)
Primer c= KT-2V:5'dCATCGAAGAGGCTCCTTAGTCAAAAGAGGACCGGAGAC GCTCTGC 3' (SEQ ID NO: 10)
Primer d= PSS-4:5'dCTAGAATTCTTATCAAGCTGACTTGGCAGGCTTGA 3'(SEQ ID NO: 4)
PKD (2 template PCR reaction)
   Template 1 = pHILS1
   Template 2 = pIGF101
Primer a= PSS-1:5'dGCCGAATTCATGTTCTCTCCAATTTTCTCCTTG 3'(SEQ ID NO: 1)
Primer b= KT-1:5'dGGAGCCTCTTCGATGAGTATGCTCCAAAGCGAAGACAGA TTGCAA 3' (SEQ ID NO: 9)
Primer c= KT-2D:5'dCATCGAAGAGGCTCCTTAGATAAAAGAGGACCGGAGAC GCTCTGC 3' (SEQ ID NO: 11)
Primer d= PSS-4:5'dCTAGAATTCTTATCAAGCTGACTTGGCAGGCTTGA 3'(SEQ ID NO: 4)
AM5 (2 template PCR reaction)
   Template 1 = pHILS1
   Template 2 = pIGF101
Primer a= PSS-1:5'dGCCGAATCATGTTCTCTCCAATTTTCTCCTTG 3'(SEQ ID NO: 1)
Primer b= AM5-1:5'dTCTTTTATCTAAGGAAGCGAAGACAGATTGCAA 3'(SEQ ID NO: 12)

TABLE 1-continued

Recombinant DNA Constructs Templates and Primers for PCR Reactions

Primer c= AM5-2:5'dTCCTTAGATAAAAGAGGACCGGAGACGCTCTGC 3'(SEQ ID NO: 13)
Primer d= PSS-4:5'dCTAGAATTCTTATCAAGCTGACTTGGCAGGCTTGA 3'(SEQ ID NO: 4)
PPSI (2 template PCR reaction)
   Template 1 = PPI plasmid DNA
   Template 2 = pIGF101
Primer a= PSS-1:5'dGCCGAATCATGTTCTCTCCAATTTTCTCCTTG 3'(SEQ ID NO: 1)
Primer b= PPI-5:5'dTCTCTTGTCCAAAGAACGCTTCTCCAGAATGTTG 3'(SEQ ID NO: 14)
Primer c= PPI-6:5'dTCTTTGGACAAGAGAGGACCGGAGACGCTCTGC 3'(SEQ ID NO: 15)
Primer d= PSS-4:5'dCTAGAATTCTTATCAAGCTGACTTGGCAGGCTTGA 3'(SEQ ID NO: 4)
PPEAI (2 template PCR reaction)
   Template 1 = PPI plasmid DNA
   Template 2 = pIGF101
Primer a= PSS-1:5'dGCCGAATTCATGTTCTCTCCAATTTTCTCCTTG 3'(SEQ ID NO: 1)
Primer b= PPEA-1:5'dGAGCGTCTCCGGTCCAGCCTCACGCTTCTCCAGAATGT
              TGTA 3'                             (SEQ ID NO: 16)
Primer c= PPEA-2:5'dATTCTGGAGAAGCGTGAGGCTGGACCGGAGACGCT
               CTGC 3'                          (SEQ ID NO: 17)
Primer d= PSS4:5'dCTAGAATTCTTATCAAGCTGACTTGGCAGGCTTGA 3'(SEQ ID NO: 4)
INV (2 template PCR reaction)
   Template 1 = genomic DNA from a *P. pastoris* transformant containing the *S. cerevisiae*
   invertase signal (Tschopp et al., Biotechnology 5:1305–1308, 1987)
   Template 2 = pIGF101
Primer a= INV-1:5'dGGCGAATTCATGCTTTTGCAAGCTTTCCTTTTC 3'(SEQ ID NO: 18)
Primer b= INV-2:5'dGAGCGTCTCCGGTCCTGCAGATATTTTGGCTGC 3'(SEQ ID NO: 19)
Primer c= IGF5-1:5'dGGACCGGAGACGCTCTGCGGGGCT 3'(SEQ ID NO: 20)
Primer d= PSS-4:5'dCTAGAATTCTTATCAAGCTGACTTGGCAGGCTTGA 3'(SEQ ID NO: 4)
INVS (2 template PCR reaction)
   Template 1 = genomic DNA from Tschopp et al., supra
   Template 2 = pIGF101
Primer a= INV-1:5'dGGCGAATTCATGCTTTTGCAAGCTTTCCTTTTC 3'(SEQ ID NO: 18)
Primer b= INV-3:5'dTCTTTTATCTAAGGATGCAGATATTTTGGCTGC 3'(SEQ ID NO: 21)
Primer c= AM5-2:5'dTCCTTAGATAAAAGAGGACCGGAGACGCTCTGC 3'(SEQ ID NO: 13)
Primer d= PSS-4:5'dCTAGAATTCTTATCAAGCTGACTTGGCAGGCTTGA 3'(SEQ ID NO: 4)
HSA (2 template PCR reaction)
   Template 1 = genomic DNA from SMD 799 (SIBIA; *P. pastoris* transformant containing the
               HSA signal and HSA pro)
   Template 2 = pIGF101
Primer a= HSA-1:5'dGGCGAATTCATGAAGTGGGTAACCTTTATTTCC 3'(SEQ ID NO: 22)
Primer b= HSA-2:5'dGAGCGTCTCCGGTCCTCGACGAAACACACCCCT 3'(SEQ ID NO: 23)
Primer c= IGF5-1:5'dGGACCGGAGACGCTCTGCGGGGCT 3'(SEQ ID NO: 20)
Primer d= PSS-4:5'dCTAGAATTCTTATCAAGCTGACTTGGCAGGCTTGA 3'(SEQ ID) NO: 4)

For all recombinants except PSS, the fragments encoding secretion sequences and IGF-I were synthesized initially in two separate primary PCR amplifications (reactions 1 and 2) as overlapping fragments that were subsequently joined in a secondary PCR amplification (FIG. 6).

The flanking primers were designed so that the resultant amplified fragment ad (two template reaction) and af (three template reaction) contain EcoR1 restriction recognition sites that border the signal, pro-, and spacer coding sequences for insertion into the pAO856 expression vector.

The PSS and PPI templates were inserted directly by DNA ligation into the pAO856 expression vector following EcoR1 digestion of the template and vector DNA (FIG. 8). All other recombinant templates were inserted into the expression vector using PPI/pAO856 vector DNA (FIG. 9). The final PCR products were cleaved with EcoR1 and XhoI and inserted by DNA ligation into EcoR1/XhoI-cleaved PPI/pAO856 DNA. This replaces the acid phosphatase signal-SFE-EKR secretion sequence and a portion of the IGF-I coding sequence in PPI with the secretion and IGF-I sequences encoded in the PCR template DNA.

The integrities of all recombinant templates constructed by PCR amplification were verified by direct nucleotide sequence analysis by conventional methods known to those skilled in the art.

A. PSS. PSS contains the signal from the *P. pastoris* acid phosphatase (PHO) gene linked directly and in frame to the mature IGF-I coding sequences using the two template PCR cloning strategy described in FIG. 4. The PHO signal was generated by PCR amplification using, as a template, pHIL-S1 plasmid DNA (EPO 0 495 208 A2), a *P. pastoris* shuttle vector containing synthetic DNA coding for the *P. pastoris* acid phosphatase signal with codons altered for optimal expression in *P. pastoris*. PSS was synthesized in a two-reaction strategy using PCR (FIG. 8). Reaction 1 uses flanking primer a and internal primer b. Reaction 2 uses flanking primer d and internal primer c. Because the internal primers are complementary, the two fragments ab and cd generated in the first amplification reactions can be fused by combining and annealing them in the secondary amplification. In PSS and all other recombinant templates containing the acid phosphatase signal sequence, an L to F substitution at amino acid 6 of the signal peptide was made by changing codon CTA (present in the native acid phosphatase gene sequence) to TCC. This mutation was incorporated into the recombinant template coding sequences by including it in primer sequence A used for PCR amplification of the signal sequence.

The PSS expression vector was assembled by treating the PHO signal/IGF-I amplified fragment with EcoR1 and joining it by DNA ligation to pAO856 DNA linearized at the unique EcoR1 restriction site (FIG. 6). Following DNA transformation of competent MC1061 *E. coli* (Dower et al. 1988. *Nucl. Acids Res.* 16:6127–6145), plasmid DNA was isolated from ampicillin-resistant bacteria (Holmes et al. 1981. *Anal. Biochem.* 114:193–197) and analyzed by restriction enzyme analysis to identify the presence and proper orientation of the PHO signal/IGF-I insert. The fidelity of the amplified regions was confirmed by direct nucleotide sequence analysis.

B. PPI. PPI contains the PHO signal and the first 25 amino acids of the mature PHO protein and the spacer element EKR containing the KR cleavage site recognized by the KEX2 protease.

PPI was synthesized in a 3 template PCR reaction (FIG. 7) in which the signal was amplified from the pHIL-S1 plasmid and the PHO SFE was amplified from *P. pastoris* genomic DNA. First, a fragment encoding the PHO signal/SFE/EKR sequence (fragment ad) was constructed in the secondary PCR reaction by joining the PCR products of reactions 1 (signal product) and 2 (SFE/EKR product) by the overlaping homology between internal primers b and c. Fragment ad was then linked to the amplified IGF-I product from reaction 3 (fragment ef) in a tertiary PCR amplification (fragment af) by the overlaping homology between the internal primers d and e (Table 1). Codons encoding the C-terminal EKR spacer sequence were incorporated in the d and e internal primers used in the PCR amplification reactions.

The cloning strategy for inserting the PHO signal/SFE/EKR/IGF-I fragment into pAO856 is the same as that described for PSS.

C. PKV, PKD, AM5, HSA, INV, INVS, PPSI, and PPEAI.

All of the other recombinant vectors were assembled in 3 fragment ligation reactions containing the appropriate secretion sequence/IGF-I amplified fragment treated with EcoR1 and XhoI, the 2.058 bp XhoI/StuI fragment from PPI, and the StuI/EcoR1 plasmid fragment from pAO856 (FIG. 9).

PKV and PKD each contain the PHO signal linked to a yeast pro sequence. PKV contains the pro sequence from the *K. lactis* killer toxin precursor protein, PKD contains the same pro sequence but with a V to D substitution (Sleep et al. 1990, *Biotechnology* 8:42–46) to possibly enhance cleavage at the neighboring KR sequence. AM5 contains a 5 amino acid SLDKR (SEQ ID NO: 44) pro sequence. Codons for each of these sequences were incorporated in the b and c internal primers used in the PCR amplification reactions for synthesis of the respective recombinant constructs.

PPSI and PPEAI are derivatives of PPI containing alternative spacer sequences between the C-terminus of the SFE and the N-terminus of IGF-I. The spacer sequence for PPSI is EKRSLDKR (SEQ ID NO:24) and is cleaved presumably by the same protease (KEX2-like protease) that recognizes and cleaves the SFE-EKR sequence in the PPI secretion sequence. The template PPEAI contains three amino acids in addition to KR in its spacer sequence. The KR sequence is recognized and cleaved by dipeptidylaminopeptidases when in the context of the alpha-mating factor spacer sequence in *S. cerevisiae*. Codons for each of the spacer sequences were incorporated in the b and c primers used in the PCR amplification reactions.

INV contains the *S. cerevisiae* invertase signal and INVS has the invertase signal with an added SLDKR (SEQ ID NO: 44) PRO sequence. Codons for SLDKR (SEQ ID NO: 44) were incorporated into the b and c internal PCR primers. HSA contains the signal and pro sequences derived from the human serum albumin precursor protein.

Example 2

Construction of Multi-Copy Expression Cassette Vectors

A substantial increase in IGF-I secretion was obtained by increasing the number of recombinant templates that were integrated in the *P. pastoris* genome from 1 to 6 copies. While 6 templates gave increased yields of IGF-I, this number is not limiting on the invention. Larger copy numbers, e.g., 10 copies, can provide increased yields of IGF-I.

Six-copy expression cassettes were synthesized in successive steps from 2-copy and then 4-copy intermediates (FIG. 10). To construct the 2-copy intermediate vector, the single-copy vector DNA was treated with either BglII and SphI, or BamH1 and SphI. The BglII/SphI DNA fragment from the first restriction digest containing the AOX-I/IGF-I gene was isolated and joined in a DNA ligation reaction to the BamH1/SphI DNA fragment isolated from the second restriction digest that also contained the AOX-I/IGF-I gene. These two fragments were joined in a DNA ligation reaction creating an expression vector with a tandem duplication of the AOX-I/IGF-I gene.

The 4-copy intermediate vector was constructed by an analogous cloning strategy using the BglII/SphI and BamH1/SphI fragments isolated from the 2-copy vector. The final 6-copy expression cassette was assembled by joining the BglII/SphI fragment isolated from the 2-copy vector to the BamH1/SphI fragment isolated from the 4-copy vector.

Example 3

Construction of Secretion Sequence/IGF-I Yeast Transformants.

A HIS4 and PEP4 double mutant of *P. pastoris* (WO 92/04363, Strain SMD1168) was used as the host strain for transformation. SMD1168 lacks the ability to endogenously synthesize histidine and is deficient in certain proteolytic activities. Vector DNA was introduced into the HIS4 locus by an additive homologous recombination event after linearization of the plasmid DNA at the StuI restriction site located within the HIS4 gene. Transformation was done using the alkali cation method (BIO 101, Inc.) and transformants were selected by their ability to grow in the absence of histidine. Histidine prototroph transformants were selected and grown in culture. Genomic DNA samples were analyzed by DNA blot hybridization to identify the site of DNA integration and the copy number of the DNA integrants. Multiple transformants for each DNA construct were selected and analyzed.

Example 4

Methods for Expressing and Measuring IGF-I Production

Yeast transformants were inoculated into 100 ml of phosphate buffered YNB media, pH 6.0, 0.5% glycerol ($A_{600}$= 0.4) and incubated at 30° C. for 3 days with vigorous shaking in triple baffled flasks. The non-transformed host strain (SMD1168) was grown in the same medium supplemented with 0.002% histidine as a negative control.

Induction of the AOX-I promoter was accomplished by adding 1 ml of methanol (1% final concentration) at 24 and 48 hour time points after inoculation. At 72 hours after inoculation, the cultures ($A_{600}$=20.0) were harvested and centrifuged at 4,000 xg for 20 minutes. The cell-free supernatants were collected and diluted by the addition of an equal volume of 0.04M acetic acid. A 0.3 ml SP550C cation exchange column was equilibrated with a 2 ml wash of 0.2M acetic acid followed by a 2 ml wash of 0.02M acetic acid. The cleared supernatants were loaded onto the columns which were then rinsed with 2 ml of 0.02M acetic acid. Fractions were eluted with 1 ml 0.05M sodium acetate containing 1M NaCl. For immunoblot analysis, the 1 ml eluates were precipitated by addition of trichloroacetic acid (TCA) to a 10% final concentration at 4° C. for 30 to 60 minutes. The precipitates were collected by centrifugation at 14,000 rpm for 15 minutes at 4° C. and resuspended in 30 µl of sample buffer (100 mM Tris-HCl, pH 6.8, 4% SDS, 10% glycerol, 2% 2-mercaptoethanol).

For immunoblot analysis (Towbin et al. *Proc. Natl. Acad. Sci. USA* 1979.76:4350–4354; Burnette *Anal. Biochem.* 1981. 112:195–203), the protein samples (15 µl ) were resolved on 20% polyacrylamide-SDS gels in a Tris-tricine buffer system (Shagger et al. 1987. *Anal. Biochem.* 166:368–379) and transferred to nitrocellulose by electroblotting in 20% methanol, 25 mM Tris, 900 mM glycine, pH 8.3. The filters were blocked for 30 to 60 minutes in 1x blotto buffer (5% non-fat dry milk, 1x TBS (25 mM Tris-HCl, pH 7.4, 138 mM NaCl,2.7 mM KCl)) and incubated with a rabbit anti-IGF polyclonal antibody (Ab 10A, 1:1,000 dilution; SIBIA) in 1x blotto buffer for 1 to 12 hours at 4° C. The filters were washed 3 times for 5 minutes each in 1x TBS and incubated with the secondary antibody, a 1:2,000 dilution of the alkaline phosphatase-conjugated goat anti-rabbit Ig antibody (BioRad) for 60 minutes. The filters were developed for 30 to 120 minutes after four washes for 5 minutes each in 1 x TBS.

IGF-I levels in the culture broths were quantitated using the Amersham Radioimmunoassay (RIA) Kit (Amersham cat. number IM.1721, Amersham Corporation, Arlington Heights, Ill.; hereby incorporated by reference) and the Amersham Amerlex-M donkey anti-rabbit reagent (Amersham cat. number RPM.510, supra). Determinations were done in triplicate for each sample according to the procedure described by the vendor.

Example 5

Results of IGF-1 Production with Single-Copy Transformants

The immunoblot and RIA data on IGF-I expression in *P. pastoris* transformants carrying the recombinant single copy constructs are summarized in Table 2. Multiple clones for each class of *P. pastoris* transformants were tested in the expression assays.

The results are presented in groups of parallel assays labelled "EXP. 1, 2, . . . " etc., which differed according to the date when the cultures were induced. Levels of IGF-I induction are dependent on a number of variables, including cell density, culture conditions, and methanol concentrations. To compare relative IGF-I production levels between groups of assays, a reference standard, *P. pastoris* SMD813 (WO 92/04363), was included in each group of assays. SMD813 is a *P. pastoris* transformant, analogous to the signal/IGF-I transformants, that contains the *S. cerevisiae* alpha-mating factor signal and pro sequence linked to mature IGF-I. The success of the alpha-mating factor signal in directing efficient secretion of heterologous proteins has been observed in many other yeast expression systems and (Brake, *Meth. Enzymology* 185:408–421, 1990) is utilized in this invention as a positive reference standard. The immunoblot scores reflect a qualitative description of the IGF-I levels relative to the highest producing transformants (+++ ++). The RIA data quantitate the levels of IGF-I in the conditioned medium at the time of harvest.

TABLE 2

| Strain | Shake Flask | | EXP. NO. |
|---|---|---|---|
| | Immunoblot (relative level) | RIA (ng/ml) | |
| SMD1168 (host strain) | – | 3 | 1 |
| SMD813 (AMF/IGF-I) | +++++ | 866 | |
| PSS142-6 | + | 30 | |
| PSS142-7 | + | 75 | |
| PPI 16-08 | +++++ | 349 | |
| PPI 16-10 | +++++ | 611 | |
| PPI 16-12 | +++++ | 643 | |
| PPI 16-13 | +++++ | 629 | |
| PPI 16-05 | +++++ | 725 | |
| PKV 13-4 | ++ | 30 | |
| PKV 13-5 | ++ | 32 | |
| PKV 13-6 | ++ | 8 | |
| PKV 13-7 | ++ | 33 | |
| PKD 2-08 | ++ | 63 | |
| PKD 2-09 | ++ | 60 | |
| PKD 2-10 | ++ | 47 | |
| AMF 2-6-1 | ++ | 6 | |
| AMF 2-6-2 | ++ | 13 | |
| AMF 2-6-4 | ++ | 24 | |
| SMD813 | +++++ | 140 | 2 |
| PPI 16-12 | +++++ | 81 | |
| HSA-19 | +++ | 46 | |
| HSA-22 | +++ | 43 | |
| HSA-23 | +++ | 47 | |
| INV-19 | ++ | 20 | |
| INV-20 | ++ | 22 | |
| SMD813 | +++++ | 145 | 3 |
| INVS-1 | ++ | 20 | |
| INVS-2 | ++ | 32 | |
| INVS-3 | ++ | 37 | |

The data of Table 2 show that either a pro sequence or a SFE is necessary for appreciable IGF-I secretion in *P. pastoris*. The amount of IGF-I secreted varies widely based on the type of SFE utilized. In general, IGF-I secretion was highest when expressed from recombinant templates that contain an SFE, and was lowest when expressed from templates with a signal with neither a pro sequence nor a SFE. Levels of IGF-I secretion with the acid phosphatase and invertase signals alone (PSS and INV, respectively) were 70 to 300-fold below the level of IGF-I secretion from the SMD813 reference standard that directs IGF-I secretion with the alpha-mating factor signal. However, IGF-I secretion in the HSA transformants, containing an HSA signal and an HSA pro sequence, were only 3-fold below SMD813. *P. pastoris* transformants containing recombinant templates with chimeric signal/SFE sequences also exhibited IGF-I secretion. IGF-I levels in the conditioned culture broth from AM5, PKV, and PKD were 150 to 500-fold below SMD813. Levels of IGF-I from INVS were 5-fold below SMD813. The overall reduced levels of IGF-I expression in the EXP. 2 and EXP. 3 groups of assays were due to low concentrations of methanol (0.1% rather than 1%) used for induction in the shake flask cultures.

Levels of IGF secretion in the PPI transformants were comparable to SMD813. Based on the results shown in Table 2, it appears that the N-terminus of the mature acid phosphatase protein is effective for directing the secretion of IGF-I in *P. pastoris*.

To verify that the secreted IGF-I was being processed properly, the N-terminal amino acid sequence was determined from IGF-I samples purified from the broth of PPI 16-10 and SMD813 cultures and blotted onto PVDF membranes. IGF-I protein samples produced from PPI 16-10 and SMD813 cultures were found to have identical and bonafide mature IGF-I N-termini. In addition, there was no evidence of alternate protein species in the isolated bands used for sequencing.

Example 6

IGF-I Production: Signal/Spacer/IGF-I Recombinants

Efficient secretion of IGF-I was also obtained with the PPI-related clones which contain additional spacer sequences between the EKR spacer sequence and the N-terminus of IGF-I (Table 3). In PPSI, the additional spacer sequence is SLDKR (SEQ ID NO: 44), and is expectedly removed by the same processing machinery that cleaves the EKR sequence. In PPEAI, the additional spacer sequence is glu-ala (EA) and it is cleaved from the following sequence by diaminopeptidases in the secretory pathway, subsequent to or coincident with removal of the SFE-EKR sequence. A positive effect of the spacer sequences on IGF-I secretion was found in at least a subset of the transformants. The IGF-I levels secreted from the PPEAI transformants were near (within 2-fold) the level obtained with the standard reference transformant SMD813. However, IGF-I levels were 2.5 to 3-fold higher than the SMD813 standard for 2 of the 3 PPSI transformants tested.

TABLE 3

| | Shake Flask | | |
|---|---|---|---|
| Strain | Immunoblot (relative level) | RIA (ng/ml) | EXP. NO. |
| SMD813 | +++++ | 624 | 1 |
| PPEAI-1 | +++++ | 311 | |
| PPEAI-2 | +++++ | 460 | |
| PPEAI-4 | +++++ | 469 | |
| SMD813 | +++++ | 706 | 2 |
| PPSI 1-1 | +++++ | 1807 | |
| PPSI 1-2 | +++++ | 1660 | |
| PPSI 1-3 | +++++ | 571 | |

N-terminal sequence analysis of secreted IGF-I from the PPSI 1—1, PPSI 1-2, and PPEAI-3 transformants showed that cleavage was occurring at the mature N-terminus of IGF-I.

Example 7

Results of IGF-I Production with Multi-Copy Transformants

One of the most important parameters in attaining high level expression of recombinant protein is the stable maintenance of multiple copies of the gene encoding the protein of interest. For large scale production, integration of the recombinant DNA into the chromosome is preferred in order to avoid DNA loss during growth of the cultures. Problems of genetic instability with episomal templates occur because selective pressure cannot be maintained in large volume cultures. What results is a reduction in episome copy number due to the selective growth advantage of plasmid-free cells. Generally, a disadvantage associated with integrative systems is low gene dosage, which in turn leads to poor expression. However, this has been overcome by the integration of multicopy cassettes of the gene encoding the recombinant protein of interest.

Efficient procedures for establishing stable integrant transformants have been developed (Cregg et al. 1985. *Mol. Cell. Biol.* 5:3376–3385; U.S. Pat. No. 4,882,279; and U.S. Pat. No. 5,135,868; all hereby incorporated by reference).

Six-copy expression cassettes were constructed for the PPI, PPSI, and PPEAI vectors and introduced into *P. pastoris* by site-directed recombination. Data on the amount of IGF-I secretion by the six-copy transformants (PPIx6, PPSIx6, and PPEAIx6) in shake flask cultures is shown in Table 4. The immunoblot scores reflect the relative levels of IGF-I in the culture broth between the 6-copy transformant cultures.

By comparing the IGF-I levels in the culture broth measured by RIA, it is clear that the increase in copy number resulted in a substantial increase in IGF-I secretion. There is significant clonal variation within each transformant group (Table 4, EXP. 1), but efficient levels of IGF-I secretion were detected for several of the transformants, namely PPSIx6–9, -10, -4, and PPEAIx6-3. Secretion efficiencies for these four transformants were less than 2-fold below that of a *P. pastoris* transformant (SMD1120) containing a 6-copy expression cassette of the AOX-I/IGF-I gene found in SMD813. The benefit of additional spacer elements is apparent by the observation that the highest IGF-I secretion levels were obtained with transformants containing cassettes with either the EKREA (SEQ ID NO: 43) or EKRSLDKR (SEQ ID NO:24) spacer sequences.

TABLE 4

| | Shake Flask | | |
|---|---|---|---|
| Strain | Immunoblot (relative level) | RIA (ng/ml) | EXP. NO. |
| SMD1120 (6-copy AMF/IGF-I) | +++++ | 28,005 | 1 |
| PPIx6-2 | +++ | 6,987 | |
| PPIx6-3 | +++ | 5,534 | |
| PPIx6-4 | ++++ | 9,781 | |
| PPSIx6-9 | ++++ | 16,744 | |
| PPSIx6-10 | ++++ | 17,450 | |
| PPSIx6-1 | ++ | 4,089 | |
| PPSIx6-2 | +++ | 4,952 | |
| PPSIx6-3 | +++ | 5,035 | |
| PPSIx6-4 | ++++ | 15,631 | |
| PPSIx6-5 | +++ | 6,131 | |
| PPEAIx6-1 | +++ | 6,505 | |
| PPEAIx6-2 | +++ | 8,822 | |
| PPEAIx6-3 | ++++ | 13,644 | |
| SMD1120 | +++++ | 15,810 | 2 |
| PPEAIx6-3 | +++++ | 11,580 | |
| PPSIx6-9 | +++++ | 13,710 | |
| PPSIx6-10 | +++++ | 6,580 | |

Considerable amounts of IGF-I were reproducibly secreted. Six copy transformants were selected from EXP. 1 and re-induced for IGF-I expression as described above. Comparable levels of IGF-I secretion were obtained for the PPSIx6-9, PPSIx6-10, and PPEAIx6-3 transformants relative to the SMD1120 reference standard (Table 4, EXP. 2 assay). These results are strongly supported by the immunoblot data presented in FIG. 11. For these high expressing transformants, a TCA-precipitate from 1 ml of conditioned culture broth (10% final concentration) was collected by centrifugation and resuspended in 50 μl of sample buffer. Aliquots of 10 μl and 5 μl were resolved by SDS-PAGE for immunoblot analysis using the Ab 10A, IGF-specific antiserum. Equivalent levels of IGF-I are detected in the conditioned broth samples from the EXP. 2 assay for PPSIx6-9, PPEAIx6-3, and SMD1120.

The results with the single and 6-copy PPI, PPSI, and PPEAI *P. pastoris* transformants demonstrate that a novel, homologous signal derived from the N-terminus of the *P. pastoris* acid phosphatase protein efficiently directs secretion of mature, properly processed IGF-I.

Example 8

Results of IGF-I Production with Multi-Copy Strains in 3-Liter Fermentations

To further evaluate IGF-I expression by the multicopy transformants, the amounts of IGF-1 produced in 3-liter fermentations were determined. Fermenters containing 1.2 L of Basal Salts medium (Table 5) were sterilized and cooled. The medium was then adjusted to pH 5.0 with ammonium hydroxide and 4 ml of a filter sterilized solution of PTM1 Trace Salts (Table 5) was added. The fermenters were inoculated with 100 ml of a culture of the transformant to be tested which was grown overnight in phosphate buffered YNB (11.5 g/L KH2PO4, 2.66 g/L K2HPO4, 6.7 g/L yeast nitrogen base, pH 6.0) with 2% glycerol to a cell density of 2 to 8 OD (absorbance at 600 nm). The pH of the resulting culture medium was maintained at 5.0 by adding ammonium hydroxide. Dissolved oxygen was maintained above 20% saturation by adjusting the agitation rate (500–1500rpm), and the levels of aeration (1–3 vvm) and oxygen feeding (0.1–0.5 vvm). Foam formation was controlled by the addition of Struktol J673 antifoam (Struktol, Stow, Ohio), and the temperature was maintained at 30° C. The first phase of the fermentation was completed when all the glycerol had been utilized in the initial medium (14–24 hours), as indicated by a sudden rise in dissolved oxygen. During this phase, cell mass typically accumulates with no expression of product. The second phase of the fermentation was then initiated by starting the addition of a solution of approximately 60% methanol/40% glycerol (by volume) containing 12ml per L of PTM1 Trace Salts, at a rate of 3.5–4 ml per hr, and adjusting the pH controller set point to 3.0. After 3–4 hours, the addition rate was increased to 7–8 ml per hr, and 2–4 hours later, the addition rate was increased to a level of 10–13 ml per hr. This addition rate was maintained throughout the remainder of the fermentation. The second phase of the fermentation typically lasts approximately 72 hours, and is the stage of the fermentation during which product is synthesized. Cell mass continues to accumulate during this phase.

TABLE 5

| Chemical | Grams/liter |
| --- | --- |
| FERMENTATION BASAL SALTS MEDIUM | |
| Phosphoric acid, 85% | (26.7 ml) |
| Calcium Sulfate | 0.93 |
| Potassium Sulfate | 18.2 |
| Magnesium Sulfate.7H$_2$O | 14.9 |
| Potassium Hydroxide | 4.13 |
| Glycerol | 20.0–40.0 |
| Water | (to a final volume of 1 Liter) |
| PTM$_1$ Trace Salts | |
| Cupric Sulfate.5H$_2$O | 6.0 |
| Sodium Iodide | 0.08 |
| Manganese Sulfate.H$_2$O | 3.0 |
| Sodium Molybdate.2H$_2$O | 0.2 |
| Boric Acid | 0.02 |
| Cobalt Chloride | 0.5 |
| Zinc Chloride | 20.0 |
| Ferrous Sulfate.7H$_2$O | 65.0 |
| Biotin | 0.2 |
| Sulfuric Acid | 5.0ml |
| Water | (to a final volume of 1 Liter) |

TABLE 5-continued

IGF-I levels in the culture broth were measured by RIA and reverse phase (RP) HPLC. For RP-HPLC analysis, fermentation samples were treated on a 0.3 ml SP Spherodex cation exchange column (Sepracor) which had been first equilibrated with 2 ml 0.2M acetic acid followed by 2 ml 0.02M acetic acid. A 4 ml cell-free sample of medium was diluted by addition of an equal volume of 0.02M acetic acid and loaded onto the 0.3 ml SP column. The column was then washed with 2 ml 0.02M acetic acid and fractions were eluted with the addition of 1 ml of 0.05M sodium acetate, pH 5.5 plus 1M NaCl. The treated fermentation fractions were then injected onto a Vydac C4 column (4.6×50 mm, Cat.# 214TP5405) at a flow rate of 1 ml per minute and were eluted in an acetonitrile gradient from 21% to 38% acetonitrile buffer over 17 minutes in 0.1% triflouroacetic acid (TFA).

The RP-HPLC assay differs from the RIA and Western blot methods since it separates the different analogs of IGF-I which are typically produced by recombinant methods. Some of these IGF-I analogs produced from recombinant cultures, including Pichia pastoris, were misfolded IGF forms, glycosylated IGF forms, multimer IGF forms (dimers and trimers), and degraded IGF forms. (Gellerfors, P. et al. 1989. J.. Biol. Chem. 264: 11444–11449; Bayne, M. L. et al. 1988. Gene 66: 235–244; IPN WO 92/04363). All these forms were immunoreactive to IGF-I antibodies, thus they contribute to the IGF-I values obtained by RIA and Western blot methods. For quantitating levels of correctly folded monomer (authentic) IGF-I, as well as the various other IGF-I analogs, standard curves were generated with a known concentration of standard authentic IGF-I.

The PPEAx6-3 strain produced the highest and most consistent IGF-I levels in the 3-Liter fermentations. In three fermentations with the PPEAx6-3 strain, final IGF-I levels of 199, 179, and 217 mg per L, as measured by RIA, were achieved. Final cell densities achieved were at 423, 618, and 478 g per L wet cell mass. The authentic IGF-I level measured for the three fermentation runs by RP-HPLC were 83, 67, and 73mg per L, whereas the total IGF-I measured by RP-HPLC were 286, 301, and 340mg per L, respectively. Table 6 shows a comparison of the RIA and RP-HPLC values obtained for the three fermentations with the PPEAx6-3 strain. There was a reasonable correlation between the RIA values and the RP-HPLC values for total IGF-I.

Also shown in Table 6 are data from fermentations carried out with the PPSI and PPI six copy strains, as well as the six copy alpha mating factor strains, AMFx6-3, and SMD1120. Expression levels with the PPSI and PPI strains reached similar levels to the PPEA strain at 179 and 195 mg per L by RIA, and 65 and 66 mg per L authentic IGF-I by RP-HPLC in one fermentation for each strain. Comparing IGF-I yields for the alpha-mating factor strain, SMD1120, RIA values of 1094 mg per L, and RP-HPLC authentic IGF-I levels of 133 mg per L were achieved. In the preferred fermentation conditions for the alpha-mating factor strains, the second phase of the fermentation was carried out with pure methanol instead of a 60% methanol/40% glycerol mixture. The IGF-I fermentation levels resulting from the pure methanol feed were determined to be from 315 to 772 mg/L by RIA, 106 to 149 mg per L for authentic IGF-I by RP-HPLC.

TABLE 6

| STRAIN | RUN # | AUTHENTIC rh-IGF mg/L | RIA rh-IGF mg/L | WET WEIGHT Cells-g/L |
|---|---|---|---|---|
| PPEAx6-3 | 41 | 83 | 199 | 423 |
| PPEAx6-3 | 48 | 67 | 179 | 618 |
| PPEAx6-3 | 59 | 73 | 217 | 478 |

TABLE 6-continued

| STRAIN | RUN # | AUTHENTIC rh-IGF mg/L | RIA rh-IGF mg/L | WET WEIGHT Cells-g/L |
|---|---|---|---|---|
| PPSIx6-9 | 49 | 65 | 116 | 603 |
| PPIx6-3 | 58 | 66 | 195 | 444 |
| SMD1120 | 75 | 133 | 1094 | 588 |
| SMD1120* | 4-3 | 110 | 315 | nd |
| SMD1120* | 11 | 106 | 398 | nd |
| SMD1120* | 62 | 149 | 772 | 451 |

*Second phase carried out with 100% methanol
nd = not determined

Other embodiments are within the following claims.

What is claimed is:

1. A recombinant DNA molecule comprising the following sequences joined in frame and in the following 5' to 3' progression:

(a) a sequence encoding a signal peptide of a secreted yeast protein;

(b) a sequence encoding at least a 5 contiguous amino acid sequence of the first 60 N-terminal amino acids of a mature yeast acid phosphatase protein; and (c) a sequence encoding a heterologous protein, wherein sequences (a) and (b) together, when positioned upstream from said sequence (c) and under the control of a functional regulatory element, bring about secretion of said heterologous protein from a host yeast cell.

2. The recombinant DNA molecule of claim 1, further comprising a sequence (d) that encodes a cleavable processing site joined in frame and 3' to said sequence (b), and in frame and 5' to said sequence (c), said cleavable processing site comprising the amino acid sequence lys-arg.

3. The recombinant DNA molecule of claim 1, further comprising a DNA sequence (d) that encodes a spacer element joined in frame and 3' to said sequence (b), and in frame and 5' to said sequence (c).

4. The recombinant DNA molecule of claim 3, wherein said spacer element is two to nine amino acids in length, inclusive, and contains a cleavable processing site.

5. The recombinant DNA molecule of claim 1, wherein said heterologous protein is insulin-like growth factor-I (IGF-I).

6. The recombinant DNA molecule of claim 1, wherein said host yeast cell is *Pichia pastoris*.

7. The recombinant DNA molecule of claim 1, wherein said molecule is integrated into the chromosome of said cell.

8. The recombinant DNA molecule of claim 7, wherein more than one copy of said molecule is integrated into said chromosome.

9. The recombinant DNA molecule of claim 1, wherein said yeast protein is acid phosphatase.

10. A recombinant DNA molecule comprising the following sequences joined in frame and in the following 5' to 3' progression:

(a) a sequence encoding a signal peptide of a yeast acid phosphatase protein;

(b) a sequence encoding a 25 contiguous amino acid sequence of the N-terminal region of a mature yeast acid phosphatase protein;

(c) a sequence encoding a spacer element which comprises a cleavable processing site; and (d) a sequence encoding insulin-like growth factor-I (IGF-I), wherein sequences (a), (b), and (c) together, when positioned upstream from said sequence (d) and under the control of a functional regulatory element, bring about secretion of said IGF-I from a host yeast cell.

11. The recombinant DNA molecule of claim 10, wherein said sequence (a) encodes a signal peptide of a *Pichia pastoris* acid phosphatase protein.

12. The recombinant DNA molecule of claim 10, wherein said sequence (b) encodes a 25 contiguous amino acid sequence of the N-terminal region of a mature *Pichia pastoris* acid phosphatase protein.

13. The recombinant DNA molecule of claim 11, wherein said sequence (b) encodes a 25 contiguous amino acid sequence of the N-terminal region of a mature *Pichia pastoris* acid phosphatase protein.

14. The recombinant DNA molecule of claim 4, wherein said sequence (e) encodes a spacer element selected from the group consisting of EKR, EKREA (SEQ ID NO: 43), EKRSLDKR (SEQ ID NO:24), and SLDKR (SEQ ID NO: 44).

15. The recombinant DNA molecule of claim 10, wherein said sequence (c) encodes a spacer element selected from the group consisting of EKR, EKREA (SEQ ID NO: 43), EKRSLDKR (SEQ ID NO:24), and SLDKR (SEQ ID NO: 44).

16. A cell comprising the recombinant DNA molecule of claim 1 or claim 8.

17. A cell comprising the recombinant DNA molecule of claim 15.

18. The cell of claim 16, wherein said cell is a yeast cell, and comprises one to ten copies, inclusive, of said recombinant DNA molecule.

\* \* \* \* \*